US 7,374,874 B2

(12) United States Patent
Walter

(10) Patent No.: US 7,374,874 B2
(45) Date of Patent: May 20, 2008

(54) **BACTERIOPHAGES THAT INFECT *BACILLUS* BACTERIA (ANTHRAX)**

(75) Inventor: Michael H. Walter, Cedar Falls, IA (US)

(73) Assignee: University of Northern Iowa Research Foundation, Cedar Falls, IA (US)

( * ) Notice: Subject to any disclaimer, the term of this patent is extended or adjusted under 35 U.S.C. 154(b) by 715 days.

(21) Appl. No.: 10/420,530

(22) Filed: Apr. 22, 2003

(65) Prior Publication Data

US 2004/0063189 A1    Apr. 1, 2004

Related U.S. Application Data

(60) Provisional application No. 60/375,301, filed on Apr. 24, 2002.

(51) Int. Cl.
| | | |
|---|---|---|
| *C12Q 1/70* | (2006.01) | |
| *C12P 21/02* | (2006.01) | |
| *C07K 1/00* | (2006.01) | |
| *A61K 8/96* | (2006.01) | |
| *A61K 38/43* | (2006.01) | |

(52) U.S. Cl. .................. 435/5; 424/50; 424/94.1; 424/93.46; 435/71.2; 530/350

(58) Field of Classification Search ............. 530/350; 424/50, 94.1, 93.46; 435/71.2, 5
See application file for complete search history.

(56) References Cited

U.S. PATENT DOCUMENTS

| | | | |
|---|---|---|---|
| 5,660,812 A | 8/1997 | Merril et al. | |
| 5,679,510 A | 10/1997 | Ray et al. | |
| 5,688,501 A | 11/1997 | Merril et al. | |
| 5,766,892 A | 6/1998 | Merril et al. | |
| 5,811,093 A | 9/1998 | Merril et al. | |
| 6,030,610 A | 2/2000 | Handelsman et al. | |
| 6,033,659 A | 3/2000 | Handelsman et al. | |
| 2004/0063189 A1 | 4/2004 | Walter | |

FOREIGN PATENT DOCUMENTS

WO    WO-2006083288 A1    8/2006

OTHER PUBLICATIONS

Attwood, T. K. ,Science vol. 290, Oct. 20, 2000.*
Biswas et al. Infection and Immunity Vo. 70, No. 1, pp. 204-210, Jan. 2002.*
Groisman et al. ,Proc. Natl. Acad. Sci., vol. 81, pp. 1480-1483, Mar. 1984.*
Walter, M. H., et al., "Destroying bacterial bio-warfare agents: growth, stability and genetic characterization of bacteriophage CP-51, lytic on *Bacillus anthracis* and *B. cereus*", *Abstracts of the General Meeting of the American Society for Microbiology*, 100, (May 2000),448.

(Continued)

*Primary Examiner*—Shanon Foley
*Assistant Examiner*—Khatol S. Shahnan-Shah
(74) *Attorney, Agent, or Firm*—Fredrikson & Byron, P.A.

(57) ABSTRACT

The invention provides bacteriophages that infect *Bacillus* bacteria, including *Bacillus anthracis*, and compositions containing the bacteriophages. The invention also provides methods for using the bacteriophages of the invention to prevent and treat infection of an organism by *Bacillus* bacteria. Methods and materials to decontaminate a surface or an organism that is contaminated with *Bacillus* bacteria or *Bacillus* spores is also provided.

18 Claims, 16 Drawing Sheets

OTHER PUBLICATIONS

Walter, M. H., "Efficacy and durability of *Bacillus anthracis* bacteriophages used against spores", *Journal of Environmental Health*, 66 (1), (Jul. 2003).
Walter, M. H., et al., "Three *Bacillus anthracis* bacteriophages from topsoil", *Current Microbiology*,47 (1), (Jul. 2003),55-58.
Weber-Dabrowska, B. , et al., "Effective phage therapy is associated with normalization of cytokine production by blood cell cultures.", *Arch Immunol Ther Exp (Warsz)*, 48(1), (2000),31-37.
Yelton, D. B., et al., "Comparison of *Bacillus cereus* bacteriophages CP-51 and CP-53", *J Virol*., 8(2), (Aug. 1971),242-253.
Yelton, D. B., et al., "Transduction in *Bacillus cereus* by each of two bacteriophages", *J Bacteriol*., 102(2):, (May 1970),573-579.
Helgason, Erlendur , et al., "*Bacillus anthracis, Bacilus cereus*, and *Bacillus thuringiensis*—one species on the basis of genetic evidence", *Applied and Environmental Microbiology*, (Jun. 2000),2627-2630.
Hughes, Jennifer B., et al., "Counting the uncountable: statistical approaches to estimating microbial diversity", *Applied and Environmental Microbiology*, (Oct. 2001),4399-4406.
Kortepeter, Mark G., et al., "Potential biological weapons threats", *Emerging Infectious Diseases*, 5(4), (1999).
Kudva, I. T., et al., "Biocontrol of *Escherichia coli* O157 with O157-specific bacteriophages", *Appl Environ Microbiol*., 65(9), (Sep. 1999),3767-3773.
Kutter, Elizabeth , "Phage therapy: bacteriophages as antibiotics: addendum", http://www.evergreen.edu/phage/polishresearch/addendu2000.htm, (2000),15 pages.
Lederberg, J , "Smaller fleas . . . ad infinitum: therapeutic bacteriophage redux", *Proc Natl Acad Sci U S A*., 93(8), (Apr. 16, 1996),3167-3168.
Leverentz, B. , et al., "Examination of bacteriophage as a biocontrol method for *Salmonella* on fresh-cut fruit: a model study", *J Food Prot 64*(8), (Aug. 2001),1116-1121.
Levin, Bruce R., et al., "Phage therapy revisited: the population biology of a bacterial infection and its treatment with bacteriophage and antibiotics", *The American Naturalist*, 147(6), (Jun. 1996),881-898.
Merril, C. R., "Bacteriophage interactions with higher organisms", *Trans N Y Acad Sci*., 36(3), (Mar. 1974),265-272.
Merril, C. R., et al., "Long-circulating bacteriophage as antibacterial agents", *Proc Natl Acad Sci U S A*., 93(8), (Apr. 16, 1996),3188-3192.
Schuch, R. , et al., "A bacteriolytic agent that detects and kills *Bacillus anthracis", Nature*, 418 (6900), (Aug. 22, 2002).
Sulakvelidze, Alexander , et al., "Bacteriophage therapy", *Antimicrob Agents Chemother 45*(3), (Mar. 2001),649-659.
Thorne, C. B., et al., "Cold lability of *Bacillus cereus* bacteriophage CP-51", *J Virol*., 14(4), (Oct. 1974),1008-1012.
Thorne, C. B., "Transduction in *Bacillus cereus* and *Bacillus anthracis", Bacteriol Rev*., 32(4 Pt 1), (Dec. 1968),358-361.
Twort, F. W., et al., "An investigation on the nature of ultra-microscopic viruses", *Lancet*, vol. II, (Dec. 4, 1915),1241-1243.
Van Regenmortel, et al., "Virus taxonomy", *7th report of the International Committee on Taxonomy of Viruses, Academic Press*, San Diego, (2000),43-52.
Van Tassel, R. L., et al., "Response of *Bacillus thuringiensis* to bacteriophage CP-51", *Can J Microbiol*., 22(4), (Apr. 1976),583-586.
Ackermann, et al., "Family podoviridae", *virus taxonomy : classification and nomenclature of viruses : seventh report of the International Committee on Taxonomy of Viruses*, SanDiego : Academic Press,(2000),106-109.
Alavidze, Z. , et al., "Isolation and characterization of lytic phages against selected *Salmonella* serotypes", *ASM 100th General Meeting*, Los Angeles, CA, (2000).
Alisky, J. , et al., "Bacteriophages show promise as antimicrobial agents", *J Infect*., 36(1), (Jan. 1998),5-15.
Barrow, P. A., et al., "Bacteriophage therapy and prophylaxis: rediscovery and renewed assessment of potential", *Trends Microbiol*., 5(7), (Jul. 1997),268-271.
Barrow, P. , et al., "Use of lytic bacteriophage for control of experimental *Escherichia coli* septicemia and meningitis in chickens and calves", *Clin Diagn Lab Immunol*., 5(3), (May 1998),294-8.
Cowles, P. B., et al., "Effect of bacteriophage on experimental anthrax in white mice", *Journal of Infectious Diseases*, 49, (1931),264-269.
Eiserling, F. A., et al., "Capsomeres and other structures observed on some bacteriophases", *Pathologia et microbiologia (Basel)*, 28, (1965),175-180.
Fitzgerald, Deborah A., "Making every nanoliter count", *The Scientist*, (Oct. 29, 2001),22-23, 26.
Fox, Jeffrey L., "Phage treatments yield healthier tomato, pepper plants", *ASM News 66*(8), (2000),455-456.
Akimkin, V. G., et al., "Practical use of adapted *Salmonella* bacteriophage for the treatment and prevention of nosocomial infections", *Zh Mikrobiol Epidemiol Immunobiol*.,(6), Article in Russian—English translation and Certification of English Translation attached (Nov.-Dec. 1998),85-6.
D'Herelle, M. F., et al., "MICROBIOLOGY—On an invisible antagonist microbe of the dysentery bacteria" Microbiologie—Sur un microbe invisible antagoniste des bacilles dysenteriques). Note of M.F. D'Herelle, presented by M. Roux, *C R Acad Ser D*, 165, Article in French—English translation and Certification of English Translation attached; (Jul.-Dec. 1917),373-375.
Regenmortel, et al., "Virus taxonomy, 7th report of the International Committee on Taxonomy of Viruses" (2000).
Sneath, Peter H., "Endospore-forming gram-positive rods and cocci", *Holt, Bergey's Manual of Systematic Bacteriology, Section 13, Baltimore, Williams & Wilkins*, (1984),1104-1121.

* cited by examiner

BACTERIOPHAGES THAT INFECT *BACILLUS* BACTERIA (ANTHRAX)

PRIORITY CLAIM

This application claims priority from U.S. provisional application Ser. No. 60/375,301, filed on Apr. 24, 2002 which is incorporated herein by reference.

FIELD OF THE INVENTION

The present invention relates generally to the field of bacteriology. More specifically, it relates to the identification and use of bacteriophages to infect, neutralize and detect *Bacillus* bacteria and spores thereof.

BACKGROUND OF THE INVENTION

The emergence of pathogenic bacteria resistant to most, if not all, currently available antimicrobial agents has become a critical problem in modern medicine. This is particularly because of the concomitant increase in immunosuppressed patients. The concern that humankind is reentering the preantibiotics era has become very real and the development of alternative antiinfection modalities has become one of the highest priorities of modern medicine and biotechnology.

Prior to the discovery and widespread use of antibiotics, it was suggested that bacterial infections could be prevented or treated by the administration of bacteriophages. Bacteriophages are bacterial viruses that invade bacterial cells and, in the case of lytic bacteriophages, disrupt bacterial metabolism and cause the bacteria to lyse (burst).

Bacteriophages have been successfully used to treat dysentery and staphylococcal skin disease. In the 1940's, Bacteriophage preparations were prepared and distributed commercially for the treatment of various infections that included abscesses, suppurating wounds, vaginitis, acute and chronic infections of the upper respiratory tract and mastoid infections. However, the efficacy of bacteriophage preparations was controversial and commercial production in most of the Western world ceased with the advent of antibiotics.

Bacteriophages have several characteristics that make them attractive therapeutic agents. Bacteriophages are highly specific, very effective in lysing targeted pathogenic bacteria and are safe, as documented by their sale and use in the United States in the 1940's. Bacteriophages are also adaptable to control newly arising bacterial threats. Their safety and adaptability make bacteriophages a valuable tool in combating the increasing threat of widespread infection by pathogenic bacteria such as *Bacillus anthracis*, the causal agent of anthrax, and multiple drug resistant bacteria that are unable to be treated with antibiotics.

Accordingly, what is needed are bacteriophages and compositions that can be used to prevent and treat infections caused by *Bacillus* bacteria, such as *Bacillus anthracis*.

SUMMARY OF THE INVENTION

The invention provides bacteriophages that can infect *Bacillus* bacteria. The invention also provides nutrient broths and pharmaceutical compositions that contain bacteriophage(s) able to infect *Bacillus* bacteria. Also provided are methods to use a bacteriophage(s) to decontaminate surfaces that are contaminated with *Bacillus* bacteria or spores from *Bacillus* bacteria. The invention also provides methods to decontaminate an organism that has been contacted with *Bacillus* bacteria or spores from *Bacillus* bacteria. Also provided are methods to prevent a *Bacillus* infection or to treat a *Bacillus* infection in an organism by contacting the organism with a bacteriophage(s) that will neutralize the bacteria. The invention further provides apparatuses and methods for detecting bacteria and bacterial spores in a sample. Biosensors are also provided that can be used to detect bacteria and bacterial spores. Also provided are kits containing a bacteriophage(s) of the invention. The invention also provides antibodies that bind to bacteriophage(s) that infect *Bacillus* bacteria and methods of use for the antibodies.

The bacteriophage(s) provided by the invention exhibit qualities that make them superior for anti-bacterial applications when compared to bacteriophages commonly found in the laboratory. These superior characteristics include a rapid latent period, long term stability, and virulence maintenance under conditions specific to anti-bacterial applications. The bacteriophage(s) provided by the invention may be used singly or as a mixture of different bacteriophages. The use of more than one type of bacteriophage disallows a bacterium from surviving by developing resistance to a single bacteriophage. The stability of the bacteriophage(s) provided by the invention allows them to be used directly or in the presence of additional carriers such as a nutrient broth or a pharmaceutical composition. Additionally, the bacteriophage(s) of the invention can be genetically engineered to produce recombinant bacteriophage(s) that exhibit characteristics that are altered from those of the wild-type bacteriophage(s). Examples of such altered characteristics include, but are not limited to, conference of drug resistance, expression of antisense messages to preselected genes, altered thermal stability, altered chemical stability or expression of gene products that are toxic to selected bacteria. Genetic manipulation of bacteriophage(s) is well known to those of skill in the art. The bacteriophage(s) of the invention infect *Bacillus* bacteria. Preferably the bacteriophage(s) of the invention infect *Bacillus anthracis*.

Accordingly, the invention provides many types of antibacterial nutrient broths that contain single or multiple bacteriophages of the invention. An antibacterial nutrient broth that contains a bacteriophage(s) of the invention allows the bacteriophage(s) to bind and infect a *Bacillus* bacterium. The antibacterial nutrient broth also allows a *Bacillus* spore to germinate to produce a *Bacillus* bacterium that can be bound and infected by a bacteriophage(s) contained within the nutrient broth. Preferably the *Bacillus* bacterium and spore is *Bacillus anthracis*. Additionally, the invention provides an antibacterial nutrient broth that contains a bacteriophage(s) that can infect a *Bacillus* bacteria and one or more other bacteriophage(s) that can infect other types of bacteria. For example, a pharmaceutical composition of the invention contains a bacteriophage specific to *Bacillus* bacteria and another bacteriophage that is specific to *Salmonella*. Antibacterial nutrient broths can be made from many types of nutrient broths that are known in the art and include, but are not limited to, terrific broth, tryptic soy broth, nutrient broth Y, Luria-Bertani broth and ZBT broth. An antibacterial nutrient broth can be tailored for use in a specific application by those of skill in the art. An antibacterial nutrient broth may also contain other pharmaceutical agents. Such pharmaceutical agents are recognized in the official United States Pharmacopeia, official Homeopathic Pharmacopeia of the United States, official National Formulary or any supplement thereof.

The invention also provides pharmaceutical compositions that contain single or multiple bacteriophages of the invention. These pharmaceutical compositions allow the bacteriophage(s) to bind and infect a *Bacillus* bacterium. The pharmaceutical compositions also allow a bacteriophage(s) to infect a *Bacillus* bacterium that germinates from a spore. Preferably the *Bacillus* bacterium and spore is *Bacillus anthracis*. Thus, the pharmaceutical compositions may be utilized to control both vegatative and mature *Bacillus* bacteria as well as *Bacillus* spores. Additionally, the invention provides pharmaceutical compositions that contain a bacteriophage(s) that can infect a *Bacillus* bacteria and one or more other bacteriophage(s) that can infect other types of bacteria. For example, a pharmaceutical composition of the invention contains a bacteriophage specific to *Bacillus* bacteria and another bacteriophage that is specific to *Salmonella*. The pharmaceutical compositions may be used for a large variety of applications and formulated in a large variety of forms well known to those of skill in the art. For example, the pharmaceutical compositions may be formulated for, but not limited to, topical, oral, vaginal, rectal, pulmonary, parenteral or injectable administration. A pharmaceutical composition can be tailored for use in a specific application by those of skill in the art. A pharmaceutical composition may also contain other pharmaceutical agents. Such pharmaceutical agents are recognized in the official United States Pharmacopeia, official Homeopathic Pharmacopeia of the United States, official National Formulary or any supplement thereof.

Also provided are methods to decontaminate an organism, such as a human, that was contaminated with *Bacillus* bacteria or with the spores of *Bacillus* bacteria. Preferably the *Bacillus* bacterium and spore is *Bacillus anthracis*. Thus, the invention also includes methods to decontaminate a surface that was contacted with a *Bacillus* bacterium or a spore from a *Bacillus* bacterium. The methods involve application of a bacteriophage(s) of the invention to the organism or surface contaminated with the *Bacillus* bacteria such that the bacteria are bound, infected and neutralized by the bacteriophage(s). Alternatively, the bacteriophage(s) may be contacted with a *Bacillus* bacterium that germinated from a *Bacillus* spore. The bacteriophage(s) may neutralize *Bacillus* bacteria through lysis (bursting) of the bacteria. Alternatively the bacteriophage(s) may neutralize *Bacillus* bacteria by causing the bacteria to become nonfunctional. For example, by causing the bacteria to become unable to replicate, infect a host, or produce a toxic product. A variety of methods are known to those of skill to manipulate a bacteriophage(s) of the invention in order to neutralize *Bacillus* bacteria. For example, recombinant techniques can be used to cause the bacteriophage(s) of the invention to express gene products that are toxic to *Bacillus* bacteria. Alternatively, the bacteriophage(s) can be engineered through recombinant techniques to produce an antisense message to a gene product required by *Bacillus* bacteria, i.e. growth, replication or infection. Many methods are known to those of skill in the art to engineer bacteriophage(s) that will neutralize bacteria such as *Bacillus*. Therefore, the scope of the invention is intended to include such engineered bacteriophage(s). The bacteriophage(s) may be administered to an organism or applied to a surface to be decontaminated either alone or in a variety of media. For example, bacteriophage(s) that are contained in an antibacterial nutrient broth or in a pharmaceutical composition may be administered to an organism or be applied to a surface. The bacteriophage(s) may be applied singly or in combination with one or more other bacteriophage(s). Examples of organisms include, but are not limited to, avians, plants and mammals, specifically humans. Examples of surfaces include, but are not limited to, buildings, furniture, vehicles and food products.

The invention also provides methods to prevent a *Bacillus* infection or to treat a *Bacillus* infection in an organism, such as a human, by contacting the organism with a bacteriophage (s) that will neutralize the *Bacillus* bacteria. Preferably the *Bacillus* bacterium and spore is *Bacillus anthracis*. The bacteriophage(s) may be administered to the organism directly, in an antibacterial nutrient broth or in a pharmaceutical composition. A single type of bacteriophage may be administered or more than one type of bacteriophage may be administered that will infect *Bacillus* bacteria. Additionally, bacteriophage(s) that infect *Bacillus* bacteria and one or more other bacteriophage(s) that infect other types of bacteria may be administered. Any organism that is susceptible to infection or infected with *Bacillus* bacteria may be treated according to the invention. Preferably the organism is a bovine. More preferably the organism is a human. The bacteriophage(s) may be administered in conjunction with other pharmaceutical agents. Such agents may be used to treat other indications associated with the *Bacillus* infection, such as wounding caused by cuts or scrapes. The pharmaceutical agents may also be administered to increase the efficiency of the treatment scheme. For example, antibiotics may be used in conjunction with the bacteriophage(s) of the invention to combat *Bacillus* bacteria or other disease causing microbes. Additionally, it is envisioned that the bacteriophage(s) may be used in conjunction with an agent that will increase the efficiency of bacterial lysis caused by bacteriophage(s) infection, such as detergents. The bacteriophage(s) of the invention by be administered by any route and in any formulation that a health care provider deems appropriate.

The invention further provides apparatuses for detecting a bacterium or a bacterial spore in a sample. Preferably the bacterium is a pathogenic bacterium. More preferably the bacterium is a *Bacillus* bacterium. Most preferably the bacterium is *Bacillus anthracis*. Preferably the bacterial spore is from a pathogenic bacterium. More preferably the bacterial spore is from a *Bacillus* bacterium. Most preferably the bacterial spore is from *Bacillus anthracis*. In one embodiment of the invention, an apparatus includes one surface to which at least two bacteriophages are bound. In another embodiment of the invention, an apparatus includes two surfaces, each having at least one bacteriophage bound thereon. In another embodiment of the invention, an apparatus has a plethora of surfaces to which bacteriophages of the invention are bound. Preferably the bacteriophages bound to the surfaces of the apparatuses are bacteriophages of the invention. The surface or surfaces are coupled to an electrically conductive material which is further coupled to a detection circuit. The detection circuit is adapted to determine the presence or absence of a bacterium or a bacterial spore. In one embodiment, the detection circuit is responsive to electrical current flow through a bacterium or bacterial spore that comes into contact with at least two bacteriophages bound to the surface or surfaces of the apparatuses. For example, in one embodiment the apparatus presents an open circuit containing at least two bacteriophages. Application of a sample containing a bacterium or a bacterial spore to the surface or surfaces of an apparatus of the invention allows at least two bacteriophages to bind the bacteria or bacterial spore and complete the electrical circuit. Completion of the electrical circuit provides for the flow of electrical current and indicates the presence of a bacterium or a bacterial spore in the applied sample. Accordingly, the apparatuses of the invention can be used to test for the presence or absence of a bacterium or a bacterial spore in a sample. Electrical current in the bound bacteria or bacterial spore is measurable using an amplifier, bridge circuit or other means. Two or more bacteriophages bound to the surface or surfaces of the apparatus may present a change in resistance, impedance, or other measurable electrical characteristic in the detector circuit. The apparatus may include an amplifier to provide an increased signal. Furthermore, the current and resistance may be measured to determine the quantity of bacteria or bacterial spores that are present in the sample.

The invention also provides apparatuses containing a liquid crystal that can be used to detect a bacterium or a bacterial spore in a sample. Examples of liquid crystals include, but are not limited to, thermotropic liquid crystals and twisted nematic liquid crystals. Preferably the bacterium is a pathogenic bacterium. More preferably the bacterium is a *Bacillus* bacterium. Most preferably the bacterium is *Bacillus anthracis*. Preferably the bacterial spore is from a pathogenic bacterium. More preferably the bacterial spore is from a *Bacillus* bacterium. Most preferably the bacterial spore is from *Bacillus anthracis*. An apparatus of the invention includes at least one liquid crystal to which at least one bacteriophage interacts or is bound. Preferably, a plurality of bacteriophages are bound to the liquid crystal. Preferably at least one bacteriophage of the invention is bound to the liquid crystal. More preferably, a plurality of bacteriophages of the invention are bound to the liquid crystal. Binding of a bacteria or a bacterial spore by a bacteriophage bound to the liquid crystal produces a detectable signal. Preferably this signal can be read using ambient light and the naked eye. More preferably, this signal can be amplified and transduced into an optical signal.

Further provided by the invention are biosensors having a detector that can be used on conjunction with a bacteriophage to detect a bacterium or a bacterial spore. Such detectors may include a piezoelectric device, an acoustic wave device, a surface plasmon resonance device, an optical fiber device or a light addressable potentiometric sensor device. Preferably the bacterium is a pathogenic bacterium. More preferably the bacterium is a *Bacillus* bacterium. Most preferably the bacterium is *Bacillus anthracis*. Preferably the bacterial spore is from a pathogenic bacterium. More preferably the bacterial spore is from a *Bacillus* bacterium. Most preferably the bacterial spore is from *Bacillus anthracis*. Preferably the bacteriophage is a bacteriophage of the invention.

Accordingly, the invention provides methods to detect the presence of bacteria or a bacterial spore in a sample. Preferably the bacterium is a pathogenic bacterium. More preferably the bacterium is a *Bacillus* bacterium. Most preferably the bacterium is *Bacillus anthracis*. Preferably the bacterial spore is from a pathogenic bacterium. More preferably the bacterial spore is from a *Bacillus* bacterium. Most preferably the bacterial spore is from *Bacillus anthracis*. The methods involve application of a sample to the surface of the apparatus of the invention and determining whether an increase in electrical current occurs within the apparatus. The sample may be applied in any fluid that allows the two or more bacteriophages, which are bound to the surface of the apparatus, to bind to a *Bacillus* bacterium or to a *Bacillus* spore. Examples of such fluids include, but are not limited to, blood, urine, mucous, water, nutrient broth, or other fluids that can be used to swipe an area suspected of being contaminated.

The invention also provides a kit containing a packaged form of bacteriophage(s) that are able to infect and neutralize a *Bacillus* bacterium. Preferably the *Bacillus* bacterium is a *Bacillus anthracis* bacterium. These packaged bacteriophage may be placed into tablets, pills, capsules or other forms that are easily transported and delivered to sites suspected of harboring *Bacillus* bacteria. Such a kit containing packaged bacteriophage(s) has utility for decontaminating sites used for the production of lethal forms of *Bacillus* bacteria such as *Bacillus anthracis* and preventing dissemination of bacteria produced within these sites. The kit may also be used to treat an area to hinder use of the area for production of *Bacillus* bacteria, particularly *Bacillus anthracis*. Accordingly, the invention also provides a method to decontaminate production facilities used to produce lethal forms of *Bacillus* bacteria and to hinder the use of an area to produce Bacillus bacteria.

Antibodies are also provided by the invention that bind to bacteriophage(s) which bind to a *Bacillus* bacteria or to a *Bacillus* spore. Preferably the Bacillus bacteria or spore is from *Bacillus anthracis*. Preferably the antibodies bind to the bacteriophage(s) provided by the invention. Preferably the antibodies are coupled to a detectable marker. These antibodies may be used to detect the presence of a Bacillus bacteria or a *Bacillus* spore in a sample. Accordingly, the invention provides methods to detect a *Bacillus* bacteria or a *Bacillus* spore through use of the antibodies of the invention. Preferably the methods are used to detect the presence of *Bacillus anthracis* or a *Bacillus anthracis* spore in a sample. Preferably the antibody used within a detection method is coupled to a detectable marker.

DEFINITIONS

A "detectable marker" means a label that can be coupled to an antibody. Examples of labels that can be coupled to an antibody of the invention include radioactivity, such as radioactive iodine; an enzyme, such as alkaline phosphatase, horseradish peroxidase or β-galactosidase; a fluorochrome, such as fluorescein or rhodamine isothiocyanate; a biosynthesis label, such as growing antibody secreting hybridomas in the presence of radioactive amino acids such that radioactivity is incorporated into the secreted antibodies; and a binding protein, such as biotin. Methods to couple a label to an antibody are well known in the art and are described in Harlow et al., Antibodies: A Laboratory Manual, page 319 (Cold Spring Harbor Pub. 1988).

A detectable marker may be used in direct methods and in indirect methods. An example of a direct method is where a labeled antibody of the invention is directly bound to a bacteriophage, thereby allowing detection of the bacteriophage. An example of an indirect method is where an antibody of the invention is coupled to biotin and bound to a bacteriophage. A label that is coupled to avidin or streptavidin is then contacted with the biotin coupled antibody to allow detection of the bacteriophage.

The terms "effective amount" and "therapeutically effective amount" are terms to identify an amount sufficient to obtain the desired physiological effect, e.g., treatment of a condition, disorder, disease and the like or reduction in symptoms of the condition, disorder, disease and the like. Such an effective amount of a bacteriophage of the invention in the context of the disclosed methods is an amount that results in reducing, reversing, ameliorating, inhibiting, and the like, Bacillus contamination or infection, or the risk of contamination or infection.

The term "neutralize" means to cause a bacterium to become non-pathogenic. For example, a bacterium may be neutralized through infection and lysis of the bacterium by a lytic bacteriophage. The bacterium may also be neutralized through infection of the bacterium by a bacteriophage that disables the bacterium from, i.e. reproducing, infecting a host, or producing a toxin.

A "nutrient broth" includes any fluid in which a bacterium can survive and multiply. Examples of a nutrient broth include Luria-Bertani medium, NZCYM medium, NZYM medium, NZM medium, Terrific Broth, SOB medium and SOC medium. Methods of preparing nutrient broth are well known in the art and are disclosed in Sambrook et al., Molecular Cloning: A Laboratory Manual, 2nd edition, Cold Spring Harbor Press, Cold Spring Harbor, N.Y. (1989)). An "antibacterial nutrient broth" is a nutrient broth that contains a bacteriophage of the invention.

"Operably-linked" refers to the association of two or more polynucleic acid fragments to form a single polynucleic acid fragment so that the function of one of the fragments is affected by the other. For example, a regulatory element is said to be "operably linked with a DNA sequence that codes for an RNA or a polypeptide if the two sequences are situated such that the regulatory element affects expression of the coding DNA sequence (i.e., that the coding sequence or functional RNA is under the transcriptional control of the promoter). Coding sequences can be operably-linked to regulatory elements in sense or antisense orientation.

A "pharmaceutical agent" is a substance that may be used in the diagnosis, cure, mitigation, treatment, or prevention of disease in a human or another animal. Such pharmaceutical agents are recognized in the official United States Pharmacopeia, official Homeopathic Pharmacopeia of the United States, official National Formulary or any supplement thereof.

Pharmaceutical agents that may be used in conjunction with the bacteriophages of the invention include, but are not limited to, vasodilators, nucleoside analogs, urinary tract agents, vaginal agents, ophthalmic agents, anti-anesthetics, prostaglandins, respiratory agents, sedatives, skin and mucous membrane agents, anti-bacterials, anti-fungals, anti-neoplastics, cardiovascular agents, anti-thrombotics, central nervous system stimulants, cholinesterase inhibitors, contraceptives, gastrointestinal agents, hormones, immunomodulators, analgesics, general or local anesthetics, anti-convulsants, anti-infectives, muscle relaxants, immunosuppressives, non-steroidal anti-inflammatory drugs (NSAIDs), (see Physicians' Desk Reference, 55 ed., 2001, Medical Economics Company, Inc., Montvale, N.J., pages 201-202). Those of skill in the art realize that the bacteriophages of the invention may be combined with many pharmaceutical agents to achieve a desired result.

A "regulatory element" is a nucleic acid sequence that participates in the transcription or translation of an operably linked nucleic acid sequence. Examples of regulatory elements include, but are not limited to, ribosome binding sites, promoters, repressor binding sites, introns, enhancers and the like. Such elements are well known in the art.

DETAILED DESCRIPTION OF THE INVENTION

Figures 1A, 1B, 1C:
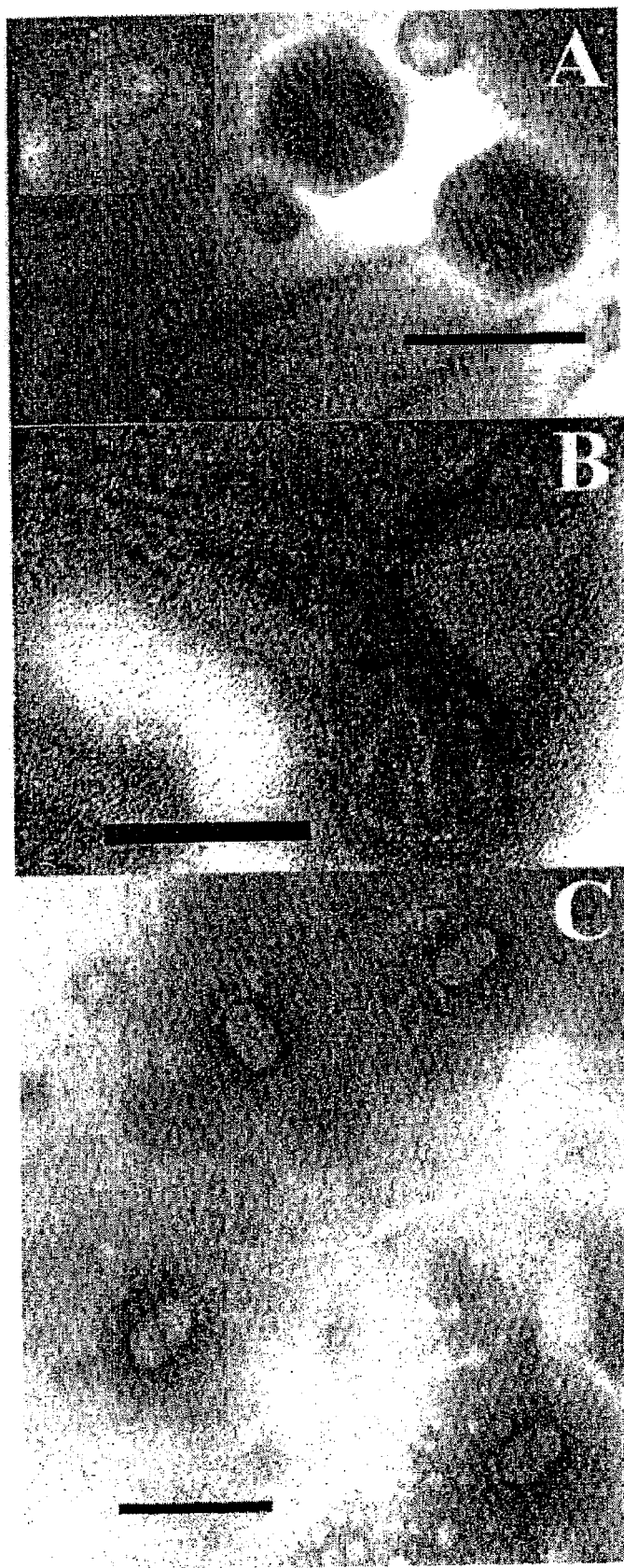
FIG. 1 illustrates the results of electron micrographs of *B. cereus* phages MHWa, NikoA and DDBa. Phage preparations were negatively stained with 1% phosphotungstate pH 7.0, observed, and images recorded in a JEOL 1200EX scanning and transmission electron microscope. Magnifications were controlled by use of catalase crystals (Luftig, 1968). Panel A features an internal standard, phage ϕ29, included with the examined sample for size reference with phage Niko. The photographic 'insert' of ϕ29 was taken from the same EM negative as the Niko image, with no alteration of magnification. Magnification of original images was at 60,000. Bar: 100 nm. A, NikoA (insert: ϕ29); B, DDBa; C, MHWa.

Early bacteriophage based anti-bacterial research included targeting *Bacillus anthracis* (the causal agent of anthrax) in mice (Cowles and Hale, *J. Inf. Dis.*, 49: 264-269 (1931)). Recent anti-bacterial applications of bacteriophages include *Salmonella* outbreaks (Akimkin et al., *Zh Mikrobiol Epidemiol Immunobiol.*, 85-86 (1998)), *Escherichia coli* O157:H7 (Kudva et al., *Appl. Environ. Microbiol.*, 65:3767-3773 (1999)) and *E. coli* in chickens and calves (Barrow et al., *Clin. Diagn. Lab. Immunol.*, 5, 294-298. (1998)). Several recent articles and reviews have focused on potential applications of bacteriophages against other dangerous bacteria (Alisky et al., *J. Infect.*, 36, 5-15 (1998); Barrow and Soothill, *Trends Microbiol.*, 5, 268-271 (1997); Lederberg, *Proc. Natl. Acad. Sci., USA*, 93: 3167-3168 (1996); Levin and Bull, *The American Naturalist*, 147: 881-898 (1996)). Many bacteriophage based anti-bacterial applications would require virulent bacteriophages with rapid latent period and long term stability under application and storage conditions. Known laboratory bacteriophage strains may not posses such characteristics, but natural sources of bacteriophage (such as soil) may contain bacteriophages much better suited for development of anti-bacterial applications.

The present disclosure describes novel bacteriophages isolated from Iowa soil that are virulent on *Bacillus* bacteria and methods for their use.

1. Bacteriophage(s) Able to Infect *Bacillus* Bacterium

The invention provides bacteriophages able to infect *Bacillus* bacterium. More specifically, the invention provides bacteriophages which are able to infect numerous species of *Bacillus* that include the pathogenic species *Bacillus anthracis*. These bacteriophages were isolated from soil samples and have been deposited on Mar. 21, 2002 under the Budapest Treaty with the American Type Culture Collection, Manassas, Virginia, U.S.A 20110-2209. The bacteriophages are named NikoA (ATCC accession number PTA-4171), DDBa (ATCC accession number PTA-4 172) and Ivil-IWa (ATCC accession number PTA-4173).

These bacteriophages are stable and are highly virulent. The growth and physical characteristics are presented for each of these bacteriophages in Table I and FIGS. 1, 2, 3, 6 and 8. The bacteriophages can also be identified based on their infectivity, protein pattern and DNA restriction digestion pattern, as presented in Table 2 and FIGS. 4, 5, 13, 14, 15, 16 and 17 respectively.

The invention also provides recombinant forms of the NikoA, DDBa and MHWa bacteriophages. FIGS. 5, 14, 15, 16 and 17 indicate that bacteriophage DNA can be readily isolated from NikoA, DDBa and MHWa and digested with common restriction enzymes under standard conditions.

Thus, bacteriophage DNA can be prepared and manipulated according to methods well known in the art.

Methods for propagation of bacteriophages and extraction of DNA from the bacteriophages are well known in the art. Also, recombinant methods for manipulating DNA isolated from bacteriophage and for producing recombinant bacteriophages are well known. Such methods are described in detail in Sambrook et al., Molecular Cloning: A Laboratory Manual, 2nd edition, Cold Spring Harbor Press, Cold Spring Harbor, N.Y. (1989)).

Briefly, the bacteriophage of the invention can be propagated in culture through infecting a suitable host, such as a *Bacillus* bacterium as disclosed in the examples herein, with a bacteriophage and allowing the bacteriophage infected host to propagate in a growth medium. Following a growth period, a bacteriophage broth may be prepared by centrifuging the growth medium to clear it of bacteria. The remaining clarified bacteriophage broth may be filter sterilized through use of a suitable commercially available filter (Millipore, Bedford, Mass.; Schleicher and Schuell, Keene, N.H.).

Bacteriophage broth may be used to infect new cultures of bacteria to produce additional bacteriophage. Additionally, bacteriophage broth may be used within the methods of the invention to decontaminate organisms and surfaces that are contaminated with *Bacillus* bacteria. Such methods include use of sterile bacteriophage broth as well as non-sterile bacteriophage broth that was produced through use of non-pathogenic strains of *Bacillus* bacteria.

Bacteriophage DNA may be prepared from the bacteriophage broth through the methods disclosed in the examples described herein. Alternatively, bacteriophage DNA may be prepared by adding polyethylene glycol to the bacteriophage broth to precipitate the bacteriophages and then collecting the bacteriophages by centrifugation. The collected bacteriophage may be further purified by centrifugation in cesium chloride. Bacteriophage DNA can be extracted from the collected bacteriophages according to methods known in the art, such as use of organic extraction or commercially available procedures (QIAGEN Inc., Chattsworth, CA).

The extracted bacteriophage DNA may be manipulated according to any procedure known in the art. Examples of such procedures include, but are not limited to, digestion with restriction enzymes, sequencing and ligation. The bacteriophage DNA may also be used as a cloning vector to insert exogenous DNA into the bacteriophage DNA to produce a recombinant molecule.

Many exogenous DNA sequences may be inserted into the bacteriophage DNA. Examples include, but are not limited to, genes that confer drug resistance, such as resistance to tetracycline, ampicillin, streptomycin or rifampicin. Also, expression cassettes containing regulatory sequences that are operably linked to a selected nucleic acid sequence may be cloned into the bacteriophage DNA. An example of such a construct would have a *Bacillus* promoter operably linked to a nucleic acid sequence that produces an antisense message to a gene required by a Bacillus bacterium. Thus, if a bacteriophage having such a construct inserted into its genome were to infect a *Bacillus* bacterium, the antisense message would be produced and would interfere with the metabolism of the bacterium. This construct is provided as an example only and one of skill in the art realizes that the invention includes many types of constructs that may be inserted into DNA obtained from the NikoA, DDBa and MHWa bacteriophages.

A recombinant bacteriophage DNA molecule may be packaged into a bacteriophage molecule by transforming the recombinant molecule into a bacterial host and then isolating recombinant bacteriophage particles that are produced. These bacteriophage particles may be selected through use of a selectable marker such as conference of drug resistance or through many other types of selective methods known in the art. Alternatively, a bacterium may be transformed with the recombinant DNA molecule and then be infected with a helper bacteriophage that will package the recombinant DNA molecule into bacteriophage particles. Such methods are routine and well known to those of skill in the art.

Bacteriophage DNA may also be isolated from bacteria that are infected with the bacteriophage. Bacteriophage DNA can often be isolated from bacteria in various forms thht are useful for various procedures that include, cloning, sequencing and mutagenesis. These forms may include double-stranded, single-strand and replicative forms of the bacteriophage DNA. Bacteriophage DNA may be isolated from bacteria through use of a variety of procedures well known in the art. Examples of these procedures include organic extraction, such as phenol:chloroform extraction, or use of column chromatography (QIAGEN Inc., Chatsworth, CA).

2. The Invention Provides Many Types of Antibacterial Nutrient Broths that Contain a Single or Multiple Bacteriophages of the Invention The invention provides an antibacterial nutrient broth in which one or more bacteriophages selected from NikoA, DDBa, MHWa, or recombinant forms thereof are contained. The invention also includes antibacterial nutrient broths containing at least one bacteriophage selected from NikoA, DDBa, MHWa or recombinant forms thereof in combination with another bacteriophage that is not NikoA, DDBa, MHWa or a recombinant form thereof.

Many nutrient broths are known to those of skill in the art for the preparation and storage of bacteriophage. Preferably the nutrient broth provides a stable storage medium for long term storage of a bacteriophage contained therein. Also, nutrient broths are preferred that provide a proper environment for the growth of *Bacillus* bacteria, preferably *Bacillus anthracis*, and infection of the *Bacillus* bacterium by a bacteriophage. Many examples of such nutrient broths are well known and include, but are not limited to, Luria-Bertani medium, NZCYM medium, NZYM medium, NZM medium, Terrific Broth, SOB medium and SOC medium. Methods for preparing nutrient broths are well known in the art and are described in Sambrook et al., Molecular Cloning: A Laboratory Manual, 2nd edition, Cold Spring Harbor Press, Cold Spring Harbor, N.Y. (1989).

The antibacterial nutrient broths of the invention may be modified to provide optimized characteristics for specific applications. Examples of such modifications include addition of antibiotics, pharmaceutical agents, salts, agents to promote bacteriophage infection of bacteria, chelating agents, agents to control viscosity and metal ions. Antibacterial nutrient broths of the invention may also be made biocompatible with an organism, such as a human, for direct application to the organism. For example, antibacterial nutrient broths may be produced that are isotonic with biological fluids, such as blood.

Methods of administration for the antibacterial nutrient broths of the invention include aerosols and infusion rectally or in surgical wounds. The antibacterial nutrient broths of the invention may also be administered to an organism in many forms that include tables, capsules, liquid preparations, sprays, aerosols, infusables, injectables and in combination with food. Those of skill in the art realize that any route of administration may be used that allows for productive infection of a bacterium by a bacteriophage.

The antibacterial nutrient broths of the invention may be used for many human and veterinary applications that include treatment of *Bacillus* infection, decontamination of *Bacillus* contaminated organisms and surfaces and prophylactic use against contraction and spread of a *Bacillus* infection.

3. The Invention also Provides Pharmaceutical Compositions that Contain a Single or Multiple Bacteriophages of the Invention The invention provides a pharmaceutical composition containing one or more bacteriophages selected from NikoA, DDBa, MHWa, or recombinant forms thereof are contained. The invention also includes pharmaceutical compositions containing at least one bacteriophage selected from NikoA, DDBa, MHWa or recombinant forms thereof in combination with another bacteriophage that is not NikoA, DDBa, MHWa or a recombinant form thereof. The invention also includes pharmaceutical compositions containing at least one bacteriophage selected from NikoA, DDBa, MHWa or a recombinant form thereof and other pharmaceutical agents that are known in the art.

The bacteriophage(s) of the invention may be administered in a powdered form in combination with additional components. The additional components can include stabilizing agents, such as salts, preservatives and antibiotics. The additional components can include nutritive components, such as those used to make a nutrient broth as described herein, or other useful components as determined by one skilled in the art.

A pharmaceutical composition includes at least one bacteriophage of the invention in combination with a pharmaceutically acceptable carrier. Examples of acceptable carriers include a solid, gelled or liquid diluent or an ingestible capsule. One or more of the bacteriophages of the invention, or a mixture thereof, may be administered orally in the form of a pharmaceutical unit dosage form comprising the bacteriophage in combination with a pharmaceutically acceptable carrier. A unit dosage of the bacteriophage may also be administered without a carrier material.

The pharmaceutical compositions of the invention may be prepared in many forms that include tablets, hard or soft gelatin capsules, aqueous solutions, suspensions, and liposomes and other slow-release formulations, such as shaped polymeric gels. An oral dosage form may be formulated such that the bacteriophage(s) of the invention are released into the intestine after passing through the stomach.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

The bacteriophages according to the invention may also be formulated for parenteral administration (e.g., by injection, for example, bolus injection or continuous infusion) and may be presented in unit dosage form in ampules, prefilled syringes, small volume infusion containers or multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the bacteriophage(s) of the invention may be in powder form, obtained by lyophilization from solution, for constitution with a suitable vehicle, e.g., sterile saline, before use. Methods for use of bacteriophage in injectable form have been described. (Merrill et al., *PNAS* (*USA*), 93:3188 (1996)).

For topical administration to the epidermis, the bacteriophage(s) may be formulated as ointments, creams or lotions. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Pharmaceutical compositions suitable for topical administration in the mouth include unit dosage forms such as lozenges comprising a bacteriophage(s) of the invention in a flavored base, usually sucrose and acadia or tragacanth. Pastilles comprising one or more bacteriophages in an inert base such as gelatin and glycerin or sucrose and acacia are also provided. Mucoadherent gels and mouthwashes comprising a bacteriophage(s) of the invention in a suitable liquid carrier are additionally provided.

Pharmaceutical compositions suitable for rectal administration are most preferably presented as unit dose suppositories. Suitable carriers include saline solution, nutrient broths, and other materials commonly used in the art. Pharmaceutical compositions suitable for vaginal administration may be presented as pessaries, tampons, creams, gels, pastes, foams or sprays that contain a carrier in addition to a bacteriophage. Such carriers are well known in the art.

For administration by inhalation, the bacteriophage(s) according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the bacteriophage(s) of the invention may take the form of a dry powder composition, for example, a powder mix of the bacteriophage(s) and a suitable powder base such as lactose or starch. The powder composition may be presented in unit dosage form in, for example, capsules or cartridges or, e.g., gelatin or blister packs from which the powder may be administered with the aid of an inhalator or insufflator. For intra-nasal administration, the bacteriophage (s) of the invention may be administered via a liquid spray, such as via a plastic bottle atomizer. For topical administration to the eye, the bacteriophage(s) according to the invention can be administered as drops and gels.

Pharmaceutical compositions of the invention may also contain other adjuvants such as flavorings, colorings, antimicrobial agents, or preservatives. The invention also provides kits containing packaging and a bacteriophage(s) of the invention.

It will be appreciated that the amount of the present bacteriophages, required for use in treatment will vary not only with the particular carrier selected but also with the route of administration, the nature of the condition being treated and the age and condition of the patient. Ultimately the attendant health care provider may determine proper dosage.

4. Methods to Prevent Contamination or to Decontaminate an Organism or Surface that may be Contaminated with *Bacillus* Bacteria or with the Spores of *Bacillus* Bacteria The invention provides methods to prevent contamination or to decontaminate an organism or a surface that may be contaminated with Bacillus bacteria or spores of *Bacillus* bacteria. The method involves contacting the organism or surface with a bacteriophage(s) of the invention such that a Bacillus bacterium, or a *Bacillus* bacterium produced by germination of a spore, present on the organism or surface will be infected by the bacteriophage(s) and neutralized.

The bacteriophage(s) of the invention may be applied to any organism that is suspected of being contaminated with a *Bacillus* bacterium or spore. Preferably the *Bacillus* bacterium or spore is *Bacillus anthracis*. It is envisioned that methods of the invention may have veterinary application toward animals used for food production, such as cattle. It is particularly envisioned that the methods of the invention may be used to decontaminate humans suspected of being exposed to *Bacillus anthracis* or to *Bacillus anthracis* spores. The methods of the invention may be used to decontaminate many surfaces that include, for example, furniture, machinery, vehicles, buildings and food products. Preferably the methods of the invention may be used to decontaminate articles that come into contact with humans. It is also envisioned that the bacteriophage(s) of the invention may be applied to foods. Examples of foods include animals and plants such as fruits, vegetables, grains, nuts and roots.

A bacteriophage selected from NikoA, DDBa, MHWa, or a recombinant form thereof may be applied to the organism or surface alone or in combination with another bacteriophage(s) or pharmaceutical agent.

One of skill in the art will recognize that a bacteriophage of the invention may be applied in a variety of forms to suite a particular circumstance. For example, the bacteriophage(s) may be applied in a powdered form to the organism such that the bacteriophage(s) will be reconstituted in the bodily fluid. The reconstituted bacteriophage(s) can then infect *Bacillus* bacterium contacting the organism or Bacillus bacteria that germinate from spores contacting the organism. Alternatively, the powdered bacteriophage(s) may be applied to an organism or surface and then reconstituted with a fluid that allows the bacteriophage(s) to infect a Bacillus bacterium present on the organism or surface or a *Bacillus* bacterium that germinates from a spore present on the organism or surface. The bacteriophage(s) of the invention may also be applied to an organism or surface while contained in a nutrient broth or pharmaceutical composition that allows the bacteriophage(s) to infect a *Bacillus* bacterium.

5. The Invention Provides Methods to Prevent a *Bacillus* Infection or to Treat a Bacillus Infection in an Organism by Contacting the Organism with a Bacteriophage(s) that will Neutralize the *Bacillus* Bacteria Causing the Infection The bacteriophages of the invention may be used to treat an organism that is infected with *Bacillus* bacteria. The method involves administering an effective amount of a bacteriophage selected from NikoA, DDBa, MHWa, or a recombinant form thereof to the organism such that the bacteriophage infects and neutralizes the Bacillus bacteria causing the infection. Preferably the *Bacillus* bacteria is *Bacillus anthracis*. The bacteriophage may be administered singly or in combination with additional bacteriophages or pharmaceutical agents.

The methods of the invention may used in a variety of circumstances that can be assessed by one of skill in the art. For example, the methods of the invention have many veterinary applications that include prevention and treatment of Bacillus infections, particularly *Bacillus anthracis*. The bacteriophage(s) of the invention may be fed or administered to animals, such as cattle, as a prophylactic measure to protect the cattle from contact with *Bacillus* bacteria or with spores from *Bacillus* bacteria. The bacteriophage(s) may be applied in many forms that include a reconstitutable powder, a nutrient broth and a pharmaceutical composition. In another embodiment, the bacteriophage(s) of the invention may be administered to animals, such as cattle, that are infected with *Bacillus* bacteria through use of methods described herein or known in the art.

The methods of the invention are particularly useful for preventing *Bacillus* infection of humans and for treating humans that are already infected with *Bacillus* bacteria, particularly *Bacillus anthracis*. Methods for treating humans and other organisms with a bacteriophage are known in the art and have been extensively described within the following documents and the documents cited therein. Sulokvelidze et al., *Antimicrobial Agents and Chemotherapy,* 45:649-659 (2001); Alisky et al., *Jour. of Infect.,* 36:5-15 (1998); Carlton R M., *Arch. Ommunol. Ther. Exp. (Warsz),* 47:267-74 (1999); Barrow et al., *Clin. Diagn. Lab. Immunol.,* 5:294-298 (1998); Markoishvili et al., *Exp. Clin. Med.,* 2:83-84 (1999); Solodovnikov et al., *Zuurnal., Mikrobiol. Epidemiol. Immunobiol.,* 47:131-137 (1970). The bacteriophage(s) of the invention can be applied to a human in many forms that include a powdered form, a nutrient broth or in a pharmaceutical composition. One skilled in the art can formulate a dosage form that will deliver an effective amount of the bacteriophage(s) to a patient in need thereof. It is envisioned that the bacteriophage(s) of the invention can be formulated to address a specific set of conditions by one skilled in the art. For example, a pharmaceutical composition may be prepared that contains a bacteriophage selected from NikoA, DDBa, MHWa, or a recombinant form thereof and an anti-inflammatory agent, an antiviral agent, an antibiotic or other such pharmaceutical agents. The bacteriophage(s) may be administered to a patient by many art recognized routes and as described herein. For example, the bacteriophage(s) may be administered orally, rectally, vaginally, topically, by injection or inhalation. In one embodiment, the bacteriophage(s) are administered to an organism, particularly a human, orally in the form of a capsule that releases the bacteriophage(s) in the intestine of the organism after passing through the stomach.

Thus, the invention includes topical and internal administration of bacteriophage(s) to animals and humans to prevent or treat infection of the animal of human by *Bacillus* bacteria, particularly *Bacillus anthracis*.

6. An Antibody that Binds to a Bacteriophage that can Bind to a Bacillus Bacterium The invention provides antibodies against bacteriophage (s) which are able to bind *Bacillus* bacteria, including the pathogenic species *Bacillus anthracis*. Such antibodies are exemplified by those that bind to the bacteriophages NikoA, DDBa, MHWa or recombinant forms thereof. The antibodies of the invention may be used in conjunction with the bacteriophage(s) of the invention to label *Bacillus* bacteria and the spores of *Bacillus* bacteria. Such labeling allows detection of Bacillus bacteria or *Bacillus* spores in a sample. The antibodies of the invention can also be used in conjunction with an apparatus for detecting *Bacillus* bacteria or Bacillus spores in a sample.

Antibodies of the invention include polyclonal antibodies, monoclonal antibodies, humanized antibodies, chimeric antibodies and fragments of antibodies. These antibodies may be coupled to a detectable marker. Examples of detectable markers include, but are not limited to, radioactivity, a fluorescent tag and an enzyme. Methods for labeling antibodies are well known in the art and are described in Harlow et al., Antibodies: A Laboratory Manual, page 319 (Cold Spring Harbor Pub. 1988)

The preparation of polyclonal antibodies is well-known to those skilled in the art. Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992).

The preparation of monoclonal antibodies is also well known in the art. Kohler & Milstein, *Nature*, 256:495 (1975); Coligan et al., sections 2.5.1-2.6.7; and Harlow et al., Antibodies: A Laboratory Manual, page 726 (Cold Spring Harbor Pub. 1988). Briefly, monoclonal antibodies can be obtained by injecting mice with a composition comprising a bacteriophage, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the bacteriophage, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. Coligan et al., sections 2.7.1-2.7.12 and sections 2.9.1-2.9.3; Barnes et al., Purification of Immunoglobulin G (IgG), in Methods in Molecular Biology, Vol. 10, pages 79-104 (Humana Press 1992).

Monoclonal antibodies may be produced in vitro through use of well known techniques. Production in vitro provides relatively pure antibody preparations and allows scale-up to yield large amounts of the desired antibodies. Large scale hybridoma cultivation can be carried out by homogenous suspension culture in an air reactor, in a continuous stirrer reactor, or immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristine tetramethylpentadecane prior to injection. After one to three weeks, the desired monoclonal antibody is recovered from the body fluid of the animal.

Alternatively, an anti-bacteriophage antibody may be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. General techniques for cloning murine immunoglobulin variable domains have been described. Orlandi et al., *PNAS (USA)*, 86:3833 (1989). Techniques for producing humanized monoclonal antibodies have also been described. Jones et al., *Nature*, 321:522 (1986); Riechmann et al., *Nature*, 332:323 (1988); Verhoeyen et al, *Science*, 239:1534 (1988); Carter et al., *PNAS (USA)*, 89:4285 (1992); Sandhu, *Crit. Rev. Biotech.*, 12:437 (1992); and Singer et al., *J. Immunol.*, 150:2844 (1993).

Antibody fragments of the invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods have been described. Goldenberg, U.S. Pat. Nos. 4,036,945 and 4,331,647; Porter, *Biochem. J.*, 73:119 (1959); Edelman et al., Methods in Enzymology, Vol. 1, page 422 (Academic Press 1967); and Coligan et al. at sections 2.8.1-2.8.10 and 2.10.1-2.10.4. Other methods of cleaving antibodies, such as separation of heavy chains to form monovalent light-heavy chain fragments, further cleavage of fragments, or other enzymatic, chemical, or genetic techniques may also be used, so long as the fragments bind to the bacteriophage that is recognized by the intact antibody.

7. Apparatuses for Detecting a Bacterium or a Bacterial Spore in a Sample

Apparatuses are provided for detecting the presence of a bacterium or a bacterial spore in a sample. In one embodiment, an apparatus include at least two bacteriophages that are connected within an electrical circuit such that contact of a bacterium or a bacterial spore with at least two of the bacteriophages will complete the electrical circuit. Completion of the electrical circuit produces a change in electrical current that indicates the presence of a bacterium or a bacterial spore in the applied sample. The apparatuses of the invention can be used to detect any bacterium or any bacterial spore to which a bacteriophage binds. Preferably the bacterium is pathogenic to humans or animals. More preferably the bacterium is a Bacillus bacterium. Most preferably the bacterium is *Bacillus anthracis*. Preferably the bacterial spore is from a pathogenic bacterium. More preferably the bacterial spore is from a *Bacillus* bacterium. Most preferably the bacterial spore is from *Bacillus anthracis*. The apparatus may include any bacteriophage that is able to bind to a bacterium or a bacterial spore, such as M13, φX174, λ phage, P1, P22, and the like. Preferably the apparatus includes at least two bacteriophages selected from NikoA, DDBa, MHWa, or a recombinant form thereof.

In one embodiment, the presence of a bacterium or a bacterial spore can be detected using an electronic detection circuit. The detection circuit may be integrated with a micro-electro mechanical system (MEMS), microfabricated circuit or nanofabricated circuit for the detection and analysis of a bacterium or a bacterial spore. The apparatus, as well as the detection circuit, may be fabricated using semiconductor fabrication techniques, methods and systems.

FIG. 7 illustrates one embodiment of the apparatus 50 of the invention. In the figure, detector circuit 75 is coupled by conductors 70A and 70B to bacteriophages 60A and 60B, which are mounted on mounting surface 65. In the embodiment shown, two bacteriophages are illustrated, however, in other embodiments, more than two bacteriophages may be present. Referring again to the figure, the bacteriophages are positioned sufficiently close to allow binding of the bacteriophages to a bacteria 55.

In one embodiment, detector circuit 75 includes user input 80, output 85, processor 90, and memory 95. Other elements may also be included, such as, for example, an amplifier to elevate the signal strength from conductors 70A and 70B. User input 80 includes user controls such as a keyboard or other data entry device. Output 85 includes a display, indicator light, audio transducer, printer, data storage device, or other output device. Processor 90, in one embodiment, includes a microprocessor and programming suitable to control the analysis and detection of bacteria or bacterial spores. Memory 95 may provide storage for test data or programming. In one embodiment, the apparatus 50 is placed into a fluid filled chamber such that bacteria or spores added to the chamber can contact bacteriophage 60A and 60B.

Figure 9:
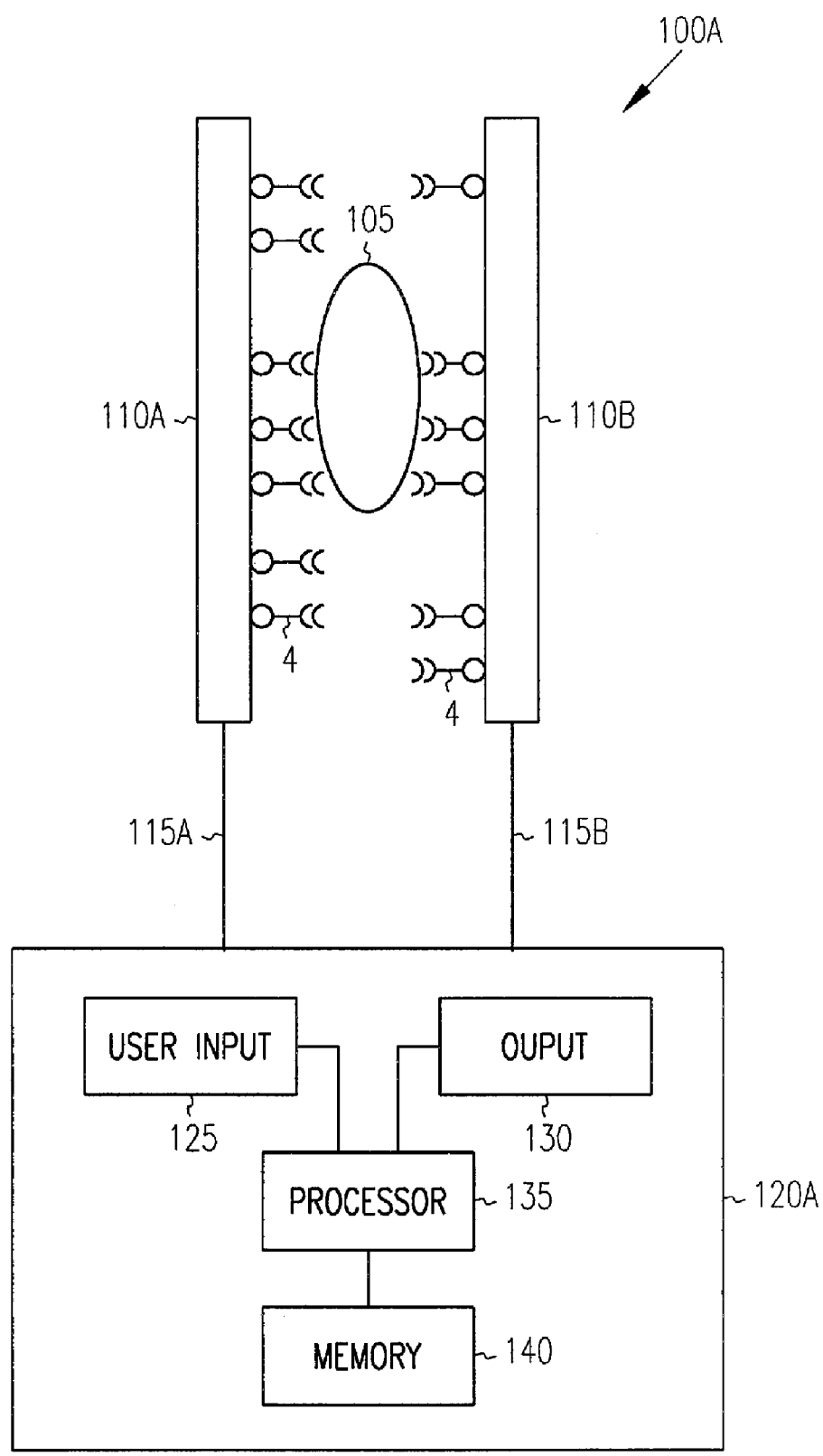
FIG. 9 illustrates one embodiment of the present system adapted to detect or analyze bacteria or spores.

FIG. 9 illustrates one embodiment of present system 100A. In the figure, detector circuit 120A is coupled by conductors 115A and 115B to contact surfaces 110A and 110B, respectively. In the embodiment shown, surfaces 110A and 110B are positioned substantially parallel, however, in other embodiments, the surfaces may be non-parallel. Non-parallel alignment may allow ingress and egress of bacteria or bacterial spores. Referring again to the figure, the inner surfaces are positioned sufficiently close to allow a bacterium or bacterial spore to migrate into the void between the surfaces and establish electrical contact with bacteriophage 4, herein shown distributed on both surfaces 110A and 110B.

In one embodiment, detector 120A includes user input 125, output 130, processor 135 and memory 140. Other elements may also be included, such as, for example, an amplifier to elevate the signal strength from surfaces 110A and 110B. User input 125 includes user controls such as a keyboard or other data entry device. Output 130 includes a display, indicator light, audio transducer, printer, data storage device or other output device. Processor 135, in one embodiment, includes a microprocessor and programming suitable to control the analysis and detection of bacteria or bacterial spores. Memory 140 may provide storage for test data or programming.

Figure 10A:
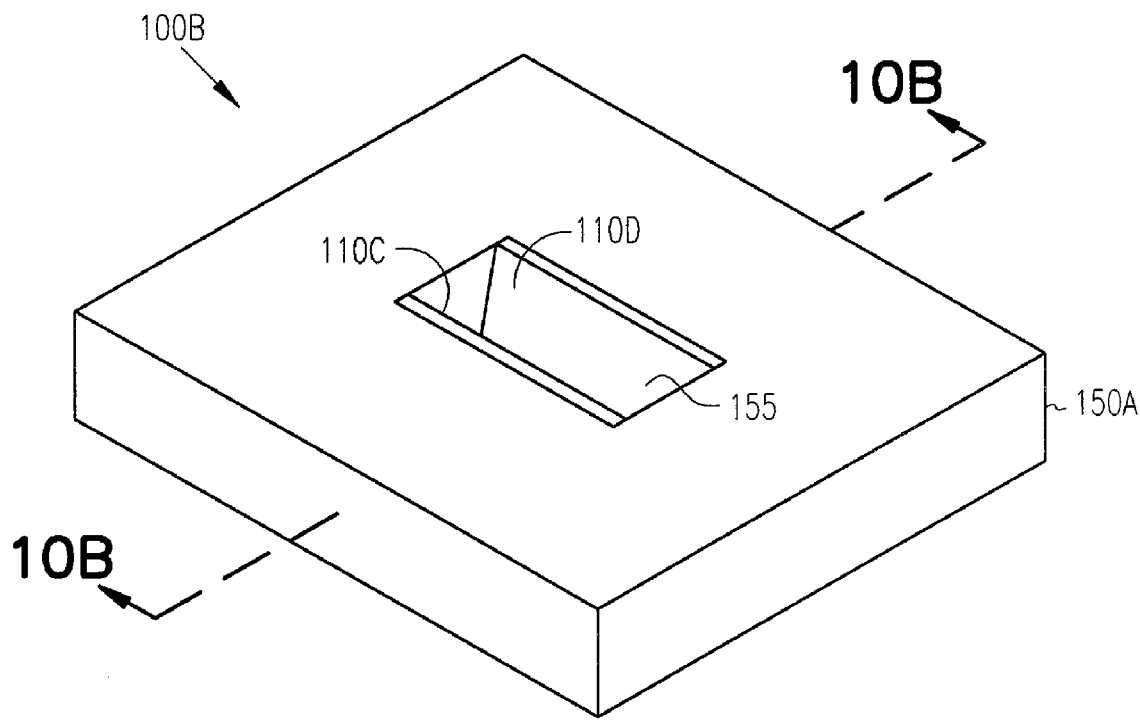
FIGS. 10A and 10B illustrate a detection apparatus according to the present system.
Figure 10B:
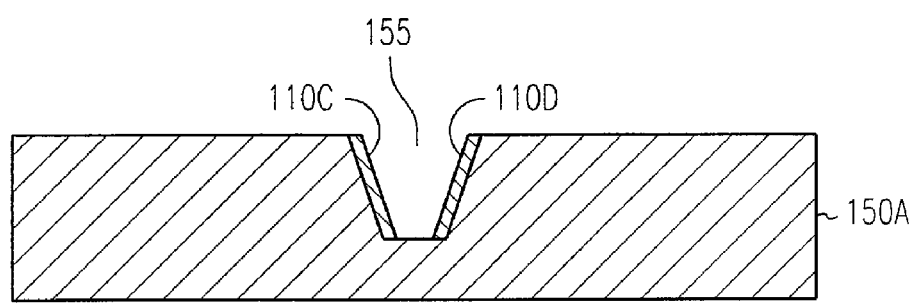

FIG. 10A illustrates a perspective view of detector apparatus 150A. Apparatus 150A includes void 155 lined on two sides with surfaces 110C and 110D. Other embodiments include conductive surfaces on more than two sides. Apparatus 150A may be fabricated using semiconductor fabrication techniques such as photolithography or nanofabrication techniques. The physical dimensions of void 155 are adapted to allow capillary action to migrate bacteria or spores into contact with surfaces 110C and 110D. FIG. 10B illustrates a view along cut-line A-A. Void 155 is illustrated to be closed on one end with a flat surface, however, in one embodiment, the surfaces 110C and 110D may be positioned to form a ridge or void 155 may be open and allow passage of fluids. An open void may allow test sample fluids to flow past surfaces 110C and 110D.

Figure 11:
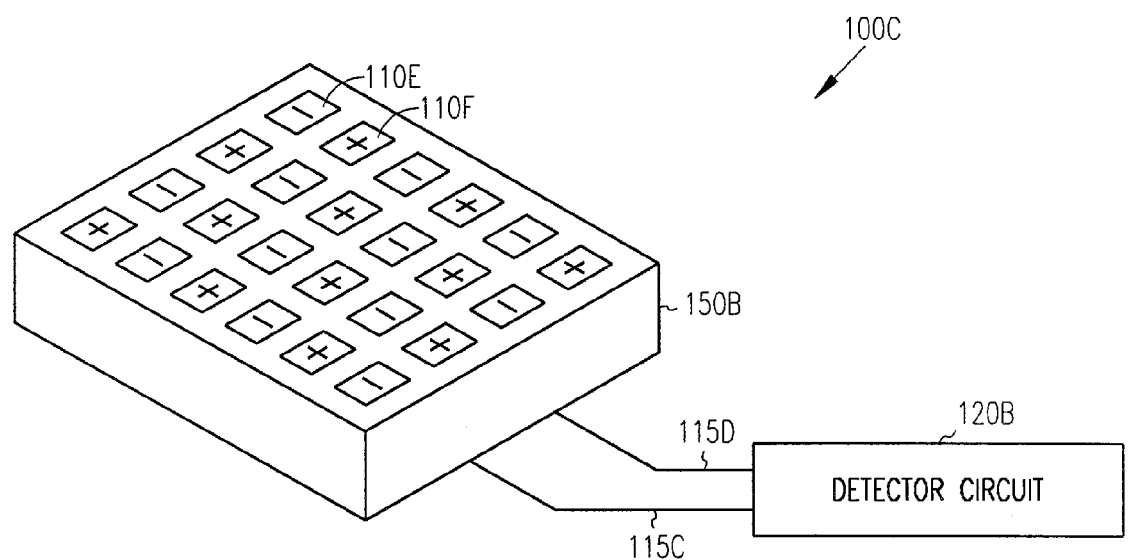
FIG. 11 illustrates a perspective view of one embodiment of a detector apparatus and a detector circuit.

FIG. 11 illustrates system 100C with a perspective view of detector apparatus 150B. Detector 150B includes a plurality of conductive surfaces, some of which are marked 110E and 110F. Surfaces 110E is marked with a "+" sign and surface 110F is marked with a "−" sign to indicate polarity. In the figure, opposite polarities exist on adjacent conductive surfaces, however, the same polarity may also be used. Conductors 115C and 115D are coupled to detector circuit 120B and to respective contact surfaces of apparatus 150B. Bacteriophage are coupled to the contact surfaces of apparatus 150B such that they may contact a bacterium or a bacterial spore that is applied to the contact surface.

Figure 12:
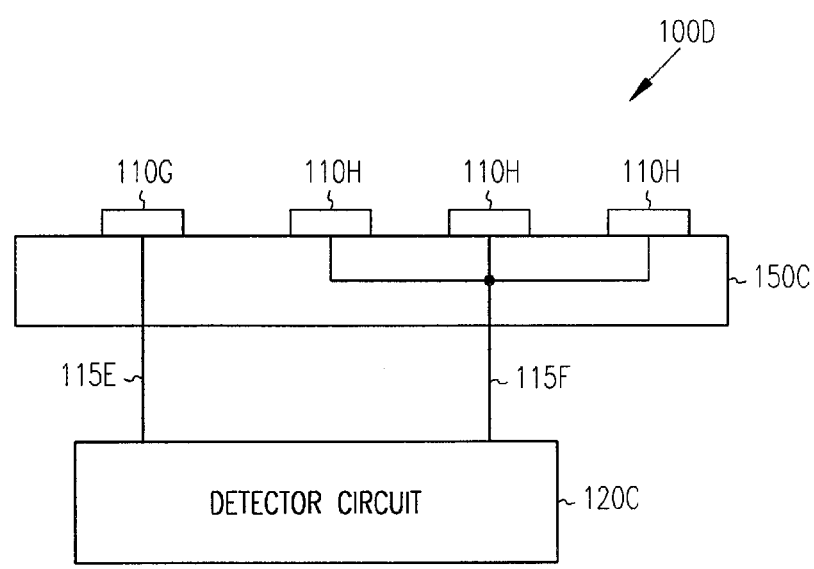
FIG. 12 illustrates an elevation view of a detector apparatus and a detector circuit.
Figure 13:
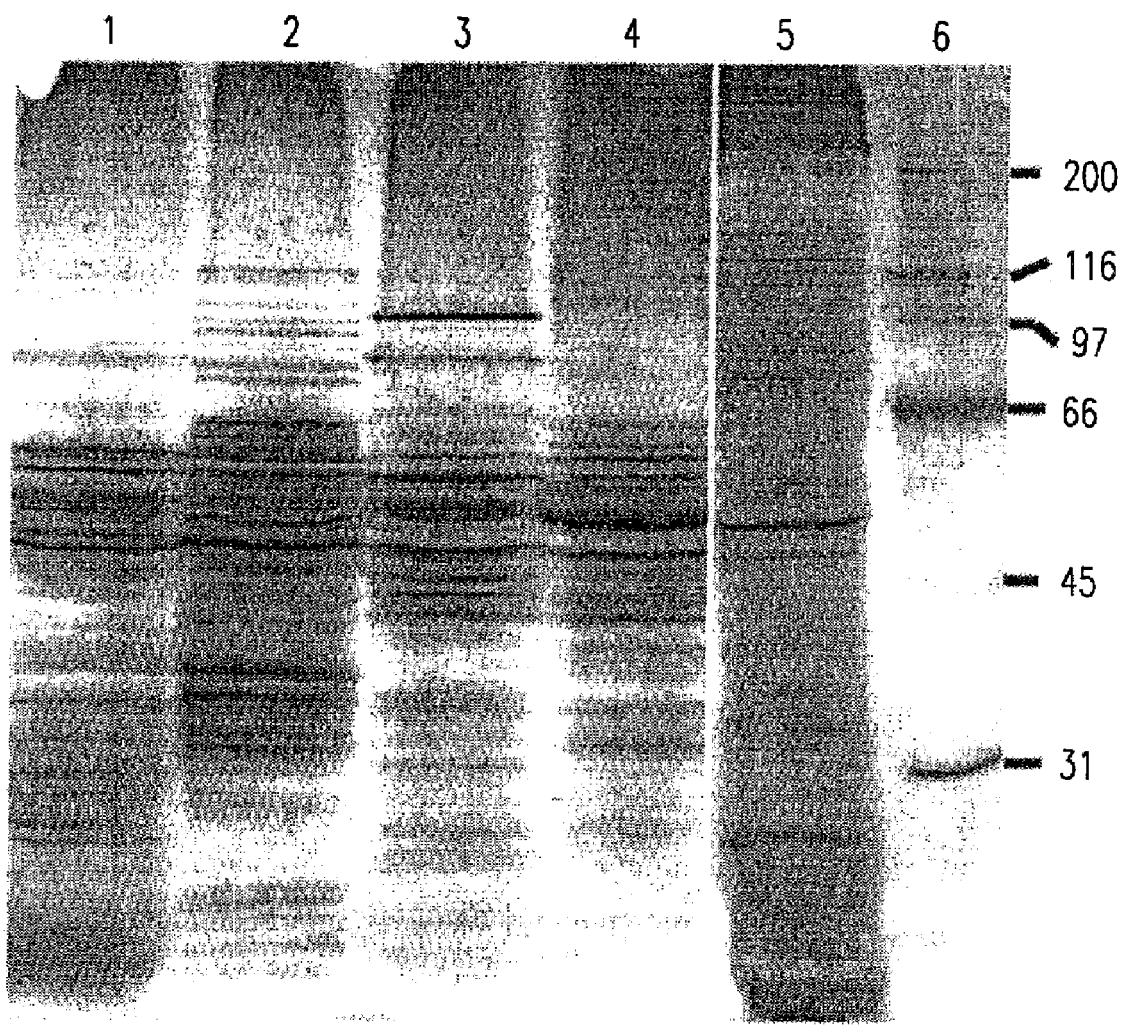
FIG. 13 illustrates differences in structural proteins of morphologically similar bacteriophages. Bacteriophages were separated as bands in approximately 1.5 g/mL cesium chloride gradients by centrifugation in a Beckman L-70 ultracentrifuge, using a SW-55 rotor at 32,000 RPM for 2 hours at 20° C. Proteins of cesium chloride-purified bacteriophages were denatured by boiling for 4 min with sodium dodecyl sulfate (SDS, Laemmli, 1970) and separated by SDS-polyacrylamide gel electrophoresis on 12.5% acrylamide gels run at 150 V (constant) for 65 min in 25 mM Tris buffer, pH 8.3. Gels were silver stained using the BioRad Silver Stain Kit (BioRad, Hercules, Calif.) according to manufacturer's instructions. Numbers at right indicate protein size in kilodaltons. Letters at top indicate lanes loaded with proteins from phages: 1, MHWa; 2, φ29; 3, NikoA; 4, DDBa; 5, SP50; and 6, protein size standards (BioRad, Silver Stain SDS-PAGE Standards High and Low Range, combined).

FIG. 12 illustrates system 100D including a view of detector apparatus 150C having contact surfaces 110G and a plurality of surfaces 110H. Apparatus 150C is coupled to detector circuit 120C by conductors 115E and 115F. Bacteriophage are coupled to surfaces 110G and 110H such that they may contact a bacterium or a bacterial spore that is applied to the detector apparatus.

In one embodiment, a detector apparatus and detector circuit are fabricated on a single chip, wafer or surface.

Consider next the operation of the present system. The presence of a bacteria or bacterial spore completes an electrical circuit including two or more bacteriophages which bind to the bacteria or bacterial spore. A change in an electrical characteristic is detected by the detector circuit. In one embodiment, the change in an electrical characteristic includes an increased current flow corresponding to the presence of a bacterium or a bacterial spore. An increase in electrical current, coinciding with the addition of a sample to the apparatus, indicates that the sample contains a bacterium or a bacterial spore. The current, or other electrical characteristic, noted following the application of a sample suspected of containing a bacterium or a bacterial spore may also be compared to that obtained following application of a control sample that does not contain a bacterium or a bacterial spore. Such a control may act to reduce or eliminate false positive results caused by any increase in conductivity due to non-bacterial components within the sample. It is particularly envisioned that the bacteriophages of the invention may be used with such an apparatus to detect the presence of *Bacillus* bacteria or Bacillus spores in a sample.

In one embodiment, a first and a second surface are placed parallel to each other. Each surface has at least one bacteriophage of the invention bound thereon. The space between the first and the second surface is sized to allow a bacterium or bacterial spore to pass between the first and second surfaces and is also great enough to prevent a bacteriophage bound to the first surface from contacting a bacteriophage bound to the second surface. The space between the first and the second surfaces is small enough to allow contact of a bacterium or bacterial spore contained between the two surfaces with a bacteriophage bound to the first surface and a bacterium bound to the second surface. Thus, a bacterium or a bacterial spore located between the first and the second surfaces will produce a measurable change in an electrical characteristic between the first and the second surfaces. For example, an electrical potential may be applied to the first surface and the second surface. Contact of a bacterium or spore with a bacteriophage bound to the first surface and a bacteriophage bound to the second surface will change the resistance, or impedance, of the detector apparatus, thus result in an increase in current flow. The increased current flow between the two surfaces can be measured. Thus, an increase in electrical current between the first surface and the second surface resulting from the application of a sample to the space between the two surfaces indicates that the sample contains at least one *Bacillus* bacterium or *Bacillus* spore.

In one embodiment, an electrical signal is delivered to the bacteria or bacterial spore via an electrical connection to one surface. A second surface is used to detect a change in the electrical signal following conduction through the bacteria or bacterial spore. In one embodiment, a resistance change, or current change, is measured based on the presence or absence of a bacterium or bacterial spore.

In addition to detecting bacterium or bacterial spores, the present system may also be used to quantify the number of bacteria or bacterial spores contained within a sample.

The bacteriophages can be attached to the surface or surfaces through direct interaction of the bacteriophages with the surface. Such interactions may include hydrophobic interactions, electrostatic interactions, or covalent bonding between molecules of the bacteriophages and the surface to which the bacteriophages will be bound. Methods to link molecules, such as proteins, to a surface are commonly used in immunosorbant assays, such as radioimmunoassays and ELISA assays. Methods to directly link a bacteriophage to a surface include, but are not limited to, use of glutaraldehyde, periodate, succinimide ester and maleimidobensoyl-N-hydroxysucinimide ester. Kitagawa and Aikawa, *J. Biochem.,* 79:233 (1976); O'Sullivan et al., *Anal. Biochem.,* 100:100 (1979); Nakane and Kawaoi, *J. Hist. Cytochem.,* 22:1084 (1974); Tijssen and Kurstak, *Anal. Biochem.,* 136:451 (1984); Avrameas and Ternynck, *Immunochemistry,* 8:1175 (1971); Avrameas, *Immunochemistry,* 6:43 (1969); Anrameas and Ternynck, *Immunochemistry,* 6:53 (1969); Bayer and Wilchek, *Meth. Biochem. Anal.,* 26:1 (1980); Bayer et al., *FEBS Lett.,* 68:240 (1976); Guesdon et al., *J. Hist. Cytochem.,* 27:1131 (1979).

Bacteriophages can also be attached to a surface of the apparatus through an antibody linkage. In this case, an antibody that binds to a bacteriophage may be linked to a surface of the apparatus. A bacteriophage is then contacted with the immobilized antibodies and is thereby bound to the surface through an antibody linkage. Alternatively, antibodies that bind to the bacteriophages of the invention can be linked to a molecule that binds to another molecule that is bound to a surface of the apparatus. For example, an antibody that binds to a bacteriophage of the invention can be coupled to biotin and used to bind a bacteriophage of the invention to a surface that is coated with avidin or streptavidin. Those of skill in the art realize that many methods may be used to bind a bacteriophage of the invention to the surface of an apparatus of the invention.

In other embodiments, the invention provides apparatuses that include a liquid crystal to which a bacteriophage is bound. Methods to manufacture liquid crystals are well known in the art and have been reported. Gupta et al., *Science,* 279:2077 (1988); S. Chandrasekhar, *Liquid Crystals* (Cambridge Univ. Press, New York, ed. 2, 1992); de Gennes and Prost, *The Physics of Liquid Crystals* (Oxford Univ. Press, New York, ed. 2, 1993)). The apparatuses can be used to determine whether or not a sample contains a bacterium or a bacterial spore. The apparatuses may include any bacteriophage that is able to bind to a bacterium or a bacterial spore, such as M13, φX174, λ phage, P1, P22, and the like. Preferably the apparatuses include a bacteriophage selected from NikoA, DDBa, MHWa, or a recombinant form thereof. Preferably the bacterium is a pathogenic bacterium. More preferably the bacterium is a *Bacillus* bacterium. Most preferably the bacterium is *Bacillus anthracis.* Preferably the bacterial spore is from a pathogenic bacterium. More preferably the bacterial spore is from a *Bacillus* bacterium. Most preferably the bacterial spore is from *Bacillus anthracis.*

In one embodiment, the liquid crystal is a thermotropic liquid crystal. Methods to make thermotropic liquid crystals have been reported and are well known in the art. Briefly, a liquid crystal cell can be made by preparing thin films of polycrystalline gold by controlled deposition to introduce an anisotropic roughness within the films. The anisotropic gold films are then coated with one or more bacteriophages. Spinke et al., *J. Chem. Phys.,* 99:7012 (1993); Prime and Whitesides, *J. Am. Chem. Soc.,* 115:10714 (1993). Liquid crystal cells are then formed by separating two coated gold films with a spacer and adding a drop of 4-cyano-4'-pentylbiphenyl into the cavity between the two films. In another embodiment, the anisotropic gold films are coated with an antibody that binds to a bacteriophage. Bacteriophage are then contacted with the antibody coated gold films to attach the bacteriophage or bacteriophages to the gold film. These gold films are then used to create liquid crystals as described above or through other techniques known in the art. Preferably the antibody used to coat the gold film is an antibody that binds to a bacteriophage the binds to a *Bacillus* bacterium, as described herein.

In another embodiment, the liquid crystal is a twisted nematic liquid crystal. The twisted nematic liquid crystal can also be patterned according to known methods such as microcontact printing. Twisted nematic liquid crystals and such patterned crystals are known in the art and have been described. (B. Bahadur, Ed., *Liquid Crystals: Applications and Uses* (World Scientific, Singapore, 1990); Gupta and Abbott, *Langmuir,* 12:2587 (1996); Gupta and Abbott, *Phys. Rev. E.,* 54:4540 (1996); Kumar et al., *Acc. Chem. Res.,* 28:219 (1995); Gupta and Abbott, *Science,* 276:1533 (1997)).

It is envisioned that the bacteriophage bound liquid crystals of the invention can be used to amplify and transduce the binding of a bacterium or a bacterial spore on the surface of the crystal into an optical output that can be read with the naked eye. The output from a liquid crystal of the invention can also be used in conjunction with additional means to modify the output. For example, a liquid crystal of the invention may be used with a microscope, amplifier, various polarizers, and the like.

Those of skill in the art recognize that liquid crystals may be made through use of a large number of techniques. Therefore, the scope of the invention includes liquid crystals manufactured through use of known techniques which have at least one bacteriophage bound thereon.

The invention also provides biosensors that utilize a bacteriophage in conjunction with a number of detectors known in the art to detect a bacterium or a bacterial spore in a sample. A bacteriophage may be coupled to a detector and used to immobilize a bacterium or a bacterial spore in a sample, thus allowing for detection of the bacterium or bacterial spore. Alternatively, a bacteriophage may be bound to a bacterium or bacterial spore that has been immobilized on the detector through use of another means, such as an antibody. The bacteriophage may be coupled to a detectable marker through methods disclosed herein and known in the art. For example, such methods may be modified from those used to couple a detectable marker to an antibody. Preferably the bacterium is a pathogenic bacterium. More preferably the bacterium is a *Bacillus* bacterium. Most preferably the bacterium is *Bacillus anthracis*. Preferably the bacterial spore is from a pathogenic bacterium. More preferably the bacterial spore is from a Bacillus bacterium. Most preferably the bacterial spore is from *Bacillus anthracis.*

Such biosensors include detectors that include piezoelectric or acoustic wave devices that detect a change in mass caused by the binding of an immobilized bacteriophage to a bacterium or to a bacterial spore. Detectors also include surface plasmon resonance devices that detect refractive index changes at the surface of thin metal films caused by binding of a bacterium or a bacterial spore to an immobilized bacteriophage. Detectors also include optical fiber devices that detect binding of a bacterium or a bacterial spore of a bacteriophage through detection of a signal, such as altered fluorescence. Light addressable potentiometric sensors may also be used as a detector through conjunction with bacteriophages to detect a bacterium or a bacterial spore in a sample. Such biosensors and methods for their use and construction have been described. Wijesuriya et al., A rapid and sensitive immunoassay for bacterial cells. In: *Proc. 1993 ERDEC Scientific Conference on Chemical Defense Research*, November 16-19, D. A. Berg, J. D. Williams and P. J. Reeves (eds.) Report No. ERDEC-SP-024, August 1994, pp. 671-677 (1994); Cao et al., *J. Clin. Microbiol.*, 33:336 (1995); Konig and Gratzel, *Anal. Letts.*, 26:1567 (1993); Paddle, *Biosensors Bioelectronics*, 11:1079 (1996); Grate et al., *Anal. Chem.*, 65:987A (1993); Fagerstam and O'Shannessy, Handbook of Affinity Chromatography, *Chromatogr. Sci. Ser.*, 63:229 (1993); Ngeh-Ngwainbi et al., *J. Am. Chem. Soc.*, 108:5444 (1986); Prusak-Sochaczewski et al., *Enzyme Microbiol. Technol.*, 12:173 (1990); North, *Trends Biotechnol.*, 3:180 (1985); Anis et al., *Anal. Letts.*, 25:627 (1992); Ogert et al., *Anal. Biochem.*, 205:306 (1992); Lee and Thompson, Fibre optic biosensor assay of Newcastle Disease Virus. *Defense Research Establishment Suffield, Canada. Suffield Report No. 580*, pp. 1-36 (1993); Parce et al., Detection of cell-affecting agents with a silicon biosensor. *Science (Washington, D.C.)*, 246:243 (1989); Owicki et al., *Ann. Rev. Biophys. Biomol. Struct.*, 23:87 (1994); Libby and Wada, *J. Clin. Microbiol.*, 27:1456 (1989).

8. Methods to Detect the Presence of Bacteria or Bacterial Spores in a Sample

The invention provides methods to detect bacteria or bacterial spores. Preferably the bacterium is a pathogenic bacterium. More preferably the bacterium is a *Bacillus* bacterium. Most preferably the bacterium is *Bacillus anthracis*. Preferably the bacterial spore is from a pathogenic bacterium. More preferably the bacterial spore is from a *Bacillus* bacterium. Most preferably the bacterial spore is from *Bacillus anthracis*. The method involves contacting a sample with an apparatus that contains at least two bacteriophages that bind to the bacterium or bacterial spore to allow an electrical current to pass through the bacterium or the bacterial spore via that two bacteriophages. The bacteriophages that can be used within the method include M13, $\phi$X174, $\lambda$ phage, P1, P22, and the like. Preferably the bacteriophages are selected from NikoA, DDBa, MHWa, or a recombinant form thereof.

In one embodiment, the presence of bacteria or bacterial spores can be determined by measuring a change in an electrical characteristic. For example, an increased electrical current may indicate the presence of a spore.

The sample may be applied to the apparatus in any manner that allows a bacterium or spore to complete an electrical circuit formed by bacteriophages attached to the apparatus of the invention. For example, the sample may be applied to the apparatus in a drop of liquid that allows a bacterium or spore to contact bacteriophages that are bound to the apparatus. A powdered sample may be applied to the apparatus and then a liquid may be added to reconstitute the sample and allow for binding of bacteriophages to a bacterium or spore. A liquid or powdered sample may also be added to liquid contained on the apparatus such that a bacterium or spore contained in the sample can contact bacteriophages bound to the apparatus. One skilled in the art can readily determine many sample compositions that may be applied to the apparatus of the invention and used to detect the presence of bacteria or spores in the sample.

Samples may be prepared from any accessible surface or organism suspected of being contaminated with bacteria. For example, samples may be obtained by swabbing a surface or organism with an absorbent material such as filter paper. Methods for obtaining biological samples are well known in the art. Biological fluids may also be used as samples within the method. Biological fluids include blood, urine, saliva and other such fluids suspected of containing bacteria or spores. Biological tissues can also be used within the method. For example, skin samples may be obtained and tested for contamination. Any sample that is obtained may be mixed with another component, such as saline, nutrient broth, a pharmaceutical composition or other components that do not interfere with binding of the bacteria or spore with bacteriophages that are bound to the apparatus.

*Bacillus* bacteria or *Bacillus* spores may also be detected through use of the bacteriophages of the invention in conjunction with an antibody of the invention.

In one example, a sample that is being tested for the presence of a Bacillus bacterium or a *Bacillus* spore is mixed with a bacteriophage that binds to the bacterium or spore to form a complex. An antibody of the invention that is coupled to a detectable marker is then contacted with the complex and thereby forms a complex containing the bacterium, bacteriophage and the coupled antibody. The unbound antibody is then separated from the complex and the presence of a Bacillus bacterium or a *Bacillus* spore is indicated by the presence of the detectable marker.

Other examples of the invention include immobilization of the antibody, the bacterium or the bacteriophage on a surface followed by addition of the other components as described above to form a detectable complex containing the bacterium, the bacteriophage and the labeled antibody. Thus, the invention includes embodiments wherein one of the components necessary to form a detectable complex is immobilized and the other components are contacted with the immobilized component to form a complex. One of skill in the art recognizes that there are many combinations and binding conditions that fall within the scope of the invention.

A sample may also be contacted with a biosensor of the invention to detect bacteria or bacterial spores present in the sample according to the methods described above and known in the art.

9. A Kit Containing a Packaged Form of Bacteriophage(s) that are Able to Infect and Neutralize *Bacillus* Bacterium A kit containing packaging material and a bacteriophage selected from NikoA, DDBa, MHWa, or a recombinant form thereof is provided by the invention. Such kits can include the bacteriophage(s) of the invention that are contained in the pharmaceutical compositions as disclosed herein.

A kit may also include packed forms of the bacteriophage (s) of the invention for decontamination of surfaces and areas. Examples of such packaged forms include containers that may be used to decontaminate an area by placing the container into the area and providing for continued release of the bacteriophage(s) from the container. Such release may be achieved through release of pressure from a pressurized container, application of a mechanical force such as a pump or through use of an explosive charge that will deliver the bacteriophage(s) to a surface. Other kits for decontamination of surfaces and areas include tablets, capsules, boxes, ampules, squeeze tubes and the like. Such kits allow delivery of a bacteriophage(s) of the invention to devices, such as fermentors, that are suspected of being contaminated with

*Bacillus* bacteria. It is particularly envisioned that the bacteria are *Bacillus anthracis*. Such packaged forms are particularly useful for decontamination of surfaces and areas because they may be delivered to a surface or area from a safe distance. This decreases the danger for personnel given the responsibility of cleaning the surface or area.

EXAMPLES

Bacteriophages and Bacteria

Bacteriophages CP-51 ts45 (from Dr. Terri Koehler, Department of Microbiology and Molecular Genetics, University of Texas-Houston Medical School), φ29 and SP50 (from Dr. H.-W. Ackermann, Department of Medical Biology, Laval University, Quebec) were purchased from collections or obtained as gifts. Bacterial host *B. cereus* 569 UM20 (from Dr. Terri Koehler, Department of Microbiology and Molecular Genetics, University of Texas-Houston Medical School, Houston, Tex.), *B. cereus* 7064, *B. cereus* 55609 (from American Type Culture Collection (Manassas, Va. 20110-2209), *B. cereus* 14579, *B. cereus* var. *mycoides* 6462, *B. megaterium* 4581, *B. thuringiensis* 13366 (from Carolina Biological Supply Co. (Burlington, N.C. 27215), *B. subtilis* HWA 1243 (from Dr. H.-W. Ackermann) and *B. anthracis* Sterne vaccine strain (from Dr. J. Jackman, Johns Hopkins University Applied Physics Lab, Laurel, Md.) were purchased from collections or obtained as gifts. All phages and host bacteria were isolated as single plaques or colonies, respectively, before growth.

Isolation and Characterization of Bacteriophages that are Able to Infect *Bacillus anthracis*

Stable, highly virulent bacteriophages were obtained by rapidly stirring 5 g of local topsoil (Black Hawk County, Iowa) in 10 mL NBY (Difco Nutrient broth: 8 g/L, Difco yeast extract (Difco Laboratories, Detroit Mich. 48232): 3 g/L, pH 6.8) with *B. cereus* 569 at 30° C. for 24 hours. Cultures were lysed and clarified by stirring with 1/10 volume chloroform (25° C. for 10 minutes) followed by low speed centrifugation at 12,100×g (10,000 RPM) for 10 minutes at 4° C. in a Beckman (Palo Alto, Calif.) model J2-HS centrifuge with a J2-20 rotor. Lysate was held at 25° C. for 24 hours to eliminate the least stable bacteriophages. Plaque assays were carried out on *B. cereus* 569 according to standard methods (Adams. M. H., *Bacteriophages*, New York, Interscience Publishers, Inc., (1959); Thorne, *J. Virol.*, 2:657-662 (1968)) and yielded numerous large plaques (>1 mm), most of which formed within 4-5 hours. Other plaques formed within 8-10 hours. Plaques were either turbid or clear and some featured concentric rings. Three plaques were picked, isolated by triple serial transfer (NikoA, DDBa, and MHWa) and grown. General characteristics of the bacteriophages are presented in Table 1.

Bacteriophages NikoA, DDBa, and MHWa were grown by standard soft agar plate lysis, modified from Thorne (SAP, Thorne, *J. Virol.*, 2:657-662 (1968)) on *B. cereus* 569. In the case of φ29 and SP50 the host was *B. subtilis* 1243. Bacteriophages NikoA, DDBa and SP50 were purified by differential centrifugation of bacterial plate lysates and consisted of two rounds of low speed centrifugation (as above) followed by 126,090×g (35,000 RPM), for 15 minutes, at 4° C. in a Beckman L-70 Ultracentrifuge, using a Type 70Ti rotor. Smaller bacteriophage (MHWa and 100 29) were purified similarly, but untracentrifugation was for 45 minutes. Bacteriophage pellets were resuspended and bacteriophages were stored in TSG buffer (10 mM Tris-HCl pH 7.5, 150 mM NaCl, 0.3% gelatin, (Carlson and Miller, Experiments in T4 genetics. In Molecular biology of bacteriophage T4. Edited by Karam, J. D. ASM Press, Washington D.C. pp. 432-433 (1994)).

CP-51 has been previously described and micrographs published (Thorne and Holt, *J. Virol.*, 14:1008-1012 (1974); Yelton and Thorne, *J. Bacteriol.*, 102:573-579 (1970)). Both DDBa and NikoA appear to belong to the family Myoviridae and may be tentatively placed in the "SP01-like virus" genus (although somewhat small for the genus) according to the most recent taxonomic key of the I.C.T.V. (van Regenmortel et al., Virus taxonomy, 7th report of the International Committee on Taxonomy of Viruses. Edited by van Regenmortel, M. H. V., Fauquet, C. M., Bishop, D. H L., Carstens, E. B., Estes, M. K., Lemon, S. M., Maniloff, J., Mayo, M. A., McGeoch, D. J., Pringle, C. R., and Wickner, R. B. Academic Press, San Diego. pp. 43-52 (2000)). Tail sheaths on about half of the NikoA bacteriophages appeared to be contracted. Many bacteriophage DDBa virions displayed a "tube" of approximately 53±9.5 nm extending beyond the base plate, also suggesting a contractile tail sheath. Bacteriophage MHWa is best placed with the "φ29-like viruses" of the Podoviridae (Ackermann and Dubow, Family Podoviridae. van Regenmortel, M. H. V., Fauquet, C. M., and Bishop, D. H. L. In Virus Taxonomy: Classification and Nomenclature of Viruses. Seventh Report of the International Committee on Taxonomy of Viruses. 7th Report, pp. 106-109 (2000)), due to its elongated head, collar appendages, noncontractile, short tail and approximately 19 kb genomic DNA (see below).

Short term stability of NikoA and DDBa was demonstrated by holding cleared lysates at 37° C. for up to 96 hours (FIG. 3) and testing for infectivity by plaque assay. MHWa was not tested because it forms a turbid plaque. The infectivity of DDBa after 96 hours decreased by only one order of magniture, while that of NikoA dropped by three orders of magnitude.

Host Range Testing

Host range tests were carried out by application of 5 µl drops of bacteriophage suspension on NBY nutrient agar plates spread with 10,000 or more cfu (colony forming units) of bacteria. Plaque formation indicated that NikoA, DDBa and MHWa were virulent on *B. anthracis* Sterne (Table 2). These results demonstrate that the tested bacteriophages are able to infect *Bacillus anthracis*. In addition to particle morphology differences, NikoA and DDBa differed from MHWa by growth on *B. cereus* 55609 and on *B. thuringiensis* 13366. In contrast to SP50, neither NikoA or DDBa infect *B. subtilis* HWA 1243. MHWa, although morphologically very similar to φ29, does not infect *B. subtilis* HWA 1243 as does φ29.

Host range tests confirmed CP-51 as a broader host range bacteriophage (Thorne, *Bacteriol Rev.*, 32:358-361 (1968); Thorne, *J. Virol.*, 2: 657-662 (1968)) and distinguished CP-51 from bacteriophages NikoA, DDBa and MHWa only on the basis of infection of *B. cereus* 7064 (Table 2). As expected, all soil bacteriophage isolates selected on UM20 were virulent on *B. anthracis* Sterne. Bacteriophages NikoA and DDBa shared host ranges and were distinguished from MHWa only on *B. cereus* 55609 and *B. thuringiensis* 13366. Neither NikoA, DDBa nor MHWa infected control *B. subtilis* HWA 1243 (host of SP50 and φ29). Although bacteriophage NikoA resembles bacteriophage SP50 (FIG. 1, Eiserling and Boy de la Tour, *Path. Microbiol.*, 28:175-180

(1965)), NikoA apparently does not infect *B. subtilis* and so is distinguished from SP-50. None of the bacteriophages grew on *B. cereus* var. *mycoides* 6462 or *B. megaterium* 4581, but all grew on *B. cereus* 14579.

Determination of Latent Period

Figure 2:
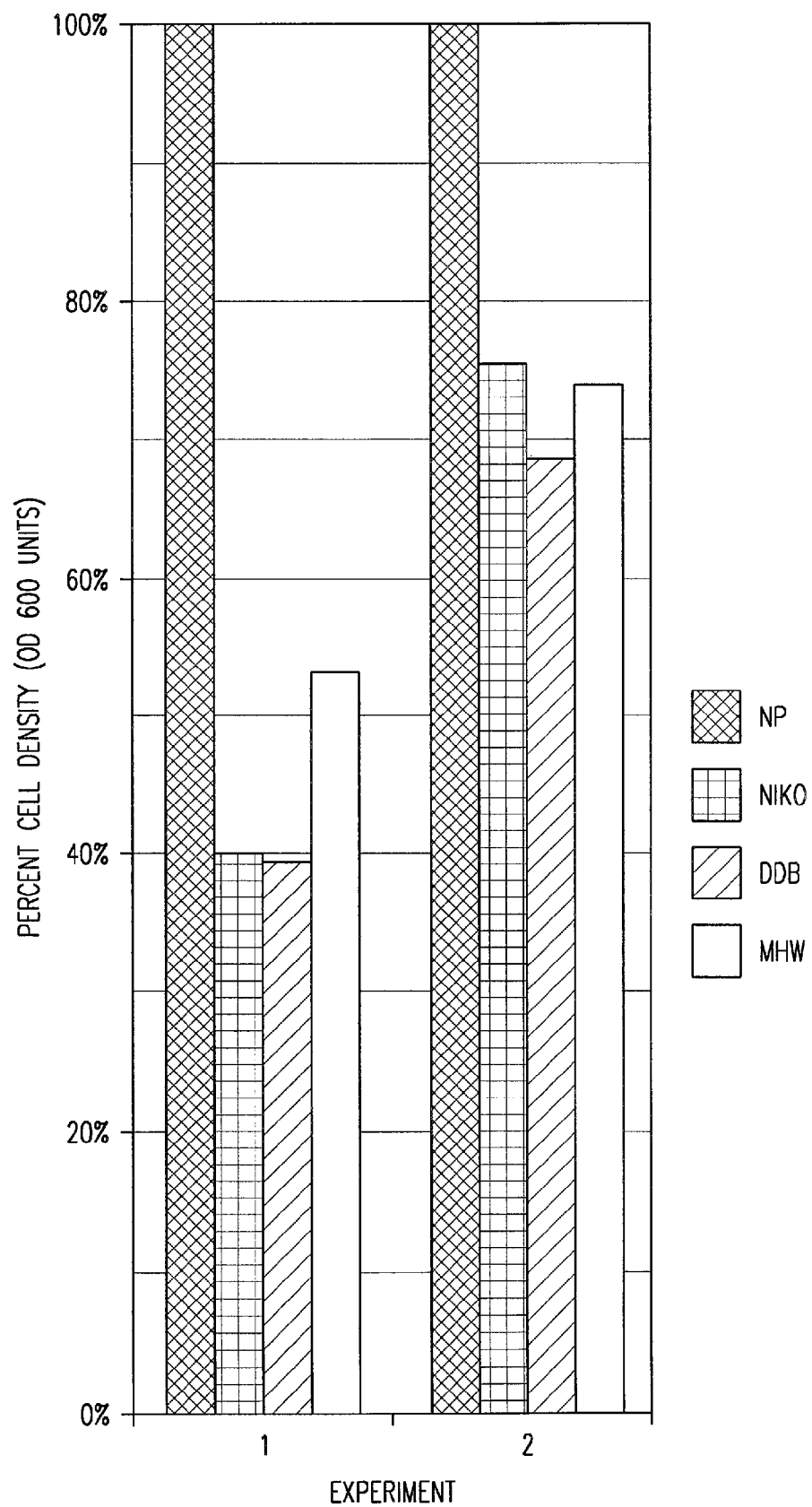
FIG. 2 represents a graph of partial culture lysis by bacteriophages NikoA, DDBa and MHWa. Early log phase cultures of *B. cereus* 569 UM20 ($A_{260}$=0.03, 2 ml) was inoculated with bacteriophages NikoA, DDBa or MHWa, briefly shaken and incubated for 4 hours at 25° C. Inoculated and control (noninoculated) cultures were monitored for changes in cell density by determination of optical density at 600 nm wavelength (using a Spectra Max Plus spectrophotometer, Molecular Devices, Sunnyvale, Calif.). 1 and 2 represent two independent experiments. NP: no bacteriophage.

Latent periods were determined by single step growth experiments carried out according to standard techniques (Carlson and Miller, Working with T4. In Molecular biology of bacteriophage T4. Edited by Karam, J. D. ASM Press, Washington D.C. pp. 421-437 (1994); Ellis and Delbrück, *J. Gen. Physiol.*, 22:365-384 (1939)). Preliminary experiments suggested that CP-51 best infected UM20 cell cultures in very early log phase ($A_{600}$=0.03). Inoculation with CP-51 (multiplicity of infection, MOI approximately 1) produced free bacteriophages at approximately 50 min. Note that *Bacillus* is frequently found in chains of cells, and so it is difficult to list MOI with close accuracy. Bacteriophages NikoA, DDBa and MHWa were released at 25-35 min after inoculation (Table 1). Bacteriophages were similarly tested for culture clearing by inoculation of 2 mL of early log phase UM20 culture with bacteriophage (MOI approximately 1), followed by brief agitation and 4 hrs incubation at 25° C. In 2 experiments, cultures were partially cleared by DDBa, NikoA and MHWa, but not by CP-51 (FIG. 2).

Plaque Assays

Figure 3:
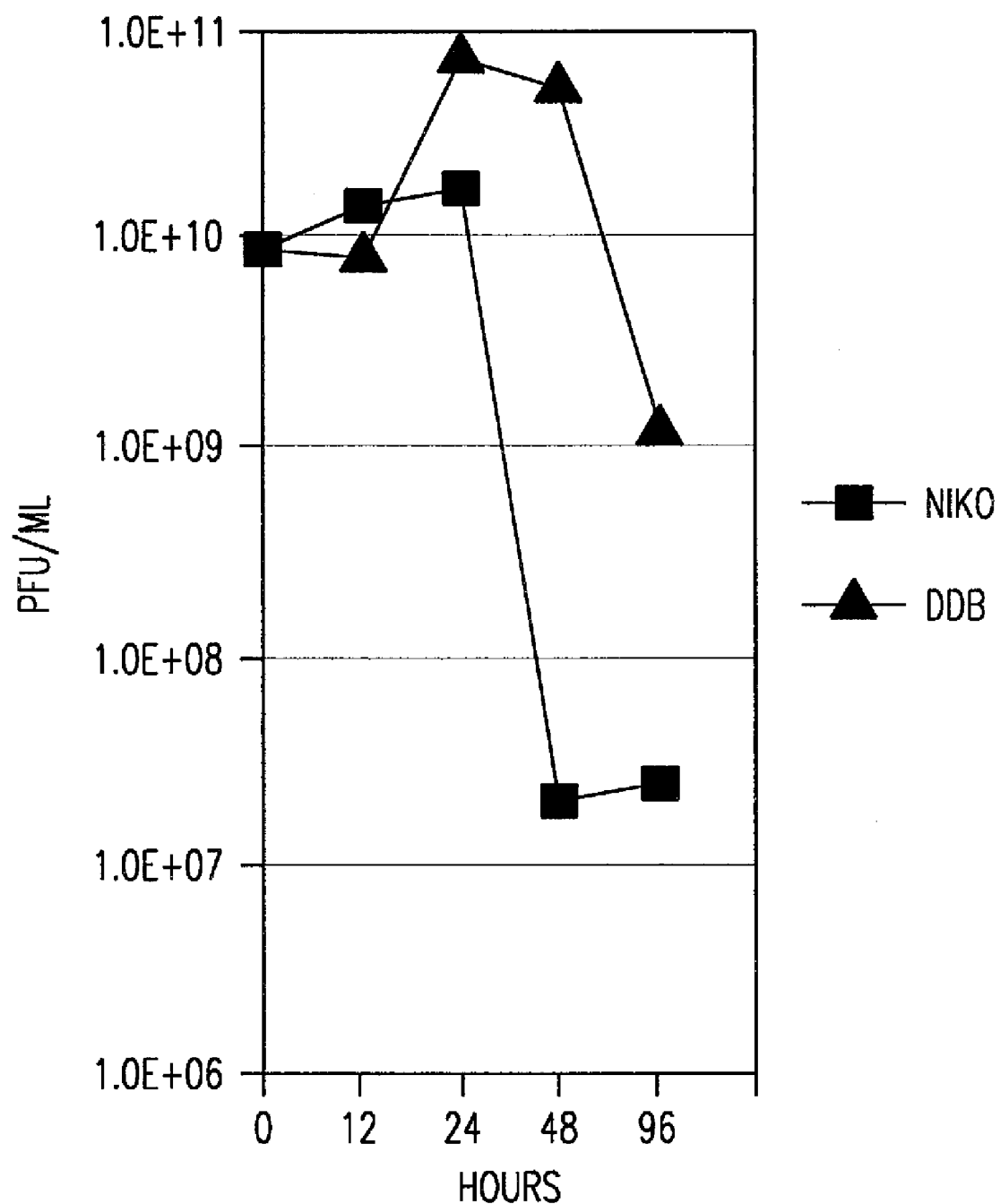
FIG. 3 represents a graph of bacteriophage stability at 37° C. Remaining infectivity (measured in plaque forming units/mL) of clear plaque forming bacteriophages NikoA and DDBa was determined by standard plaque assay following incubation of high titre lysates at 37° C. for 0 to 96 hours.

Turbid and clear plaques were observed in varying proportions in nearly all original sub-isolates of CP-51, yet different particle morphologies were never observed in electron micrographs (not shown). Clear (CP-51c) and turbid (CP-51t) plaque isolates were separated as stable isolates by serial transfer and both types increased for protein and DNA comparison (see below). Previous investigations of cold temperature instability of CP-51 were extended (Thorne and Holt, *J. Virol.*, 14:1008-1012 (1974); Van Tassel and Yousten, *Can. J. Microbiol.*, 22:583-586 (1976)). Bacteriophage ($10^4$ pfu) were incubated in 200 µL of tryptic soy broth (Difco) containing 20 mg/mL CAA and various concentrations of $Mg^{++}$, $Mn^{++}$ or $Ca^{++}$ for 2 h at 0, 4 or 17° C., followed by plaque assay. Previously published tests of divalent cation concentrations were limited to 10 mM $Mg^{++}$ treatments (Thorne and Holt, *J. Virol.*, 14:1008-1012 (1974)). It was determined that 50 mM $Mg^{++}$ or $Mn^{++}$ best maintained most bacteriophage infectivity during 0° C. and 4° C. storage. No additive effect was observed for combinations of divalents. Additionally, the infective stability of NikoA and DDBa was determined by holding bacteriophages NikoA or DDBa (as cleared lysates) at 37° C. for several days (FIG. 3).

Bacteriophage Lysis of Liquid Host Cell Cultures

Bacteriophages were tested for the ability to lyse (clear) liquid host cell cultures by inoculation of 2 ml of early log phase UM20 cells ($A_{600}$=0.03) with bacteriophages (MOI approximately 1), followed by brief agitation and 5 hours incubation at 25° C. Inoculated and control (noninoculated) cultures were monitored for changes in cell density by determination of optical density at 600 nm wavelength using a Spectra Max Plus spectrophotometer (Molecular Devices, Sunnyvale, Calif.). In 2 experiments, cell density decreased in cultures (indicating partial lysis) inoculated with NikoA, DDBa or MHWa (FIG. 2) compared to noninoculated controls.

Bacteriophage Resilience Under Various Conditions

Figure 6:
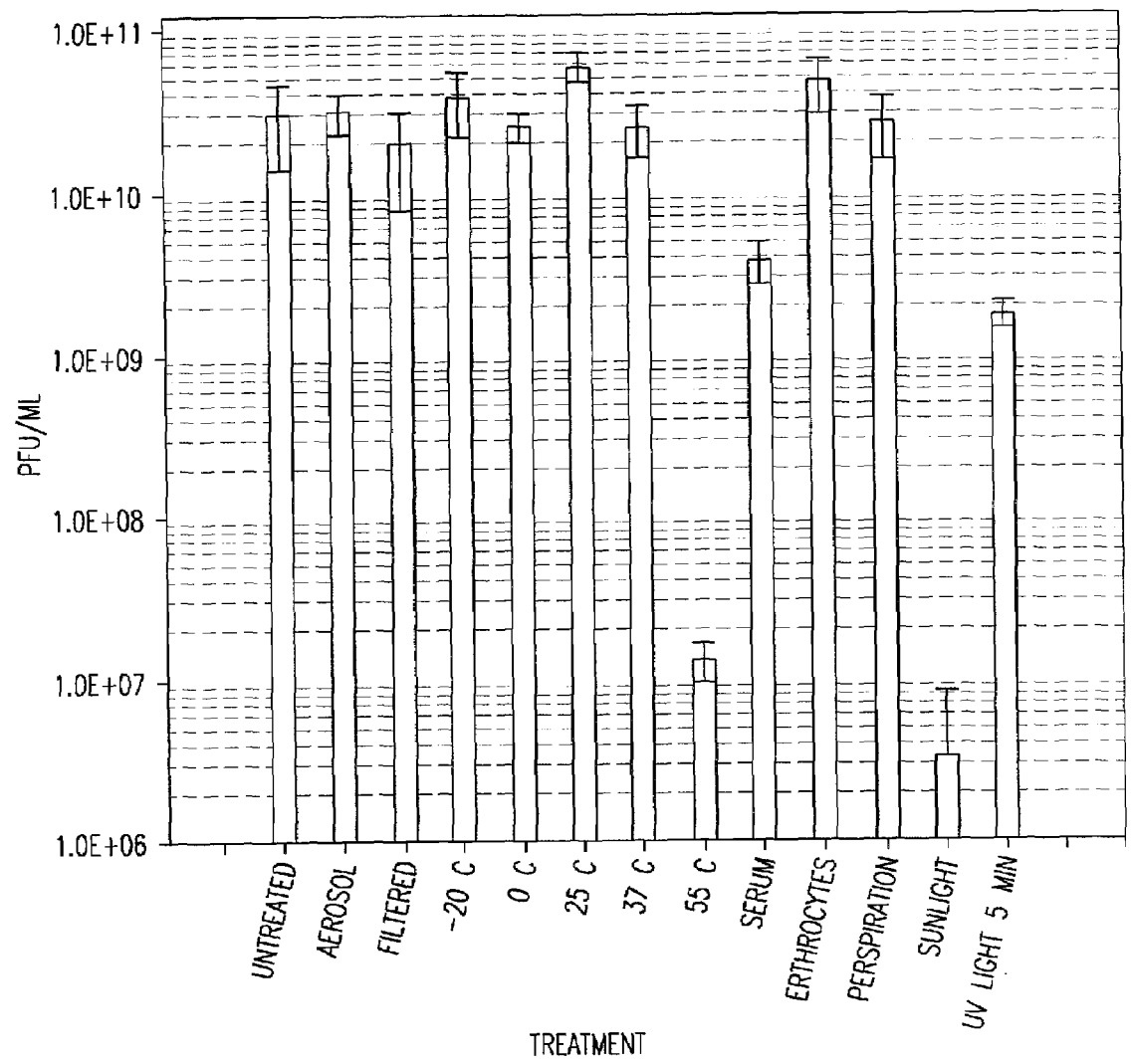
FIG. 6 illustrates the effect of various treatments on infectivity of bacteriophage community lysate. Bars=standard deviation.
Figure 7:
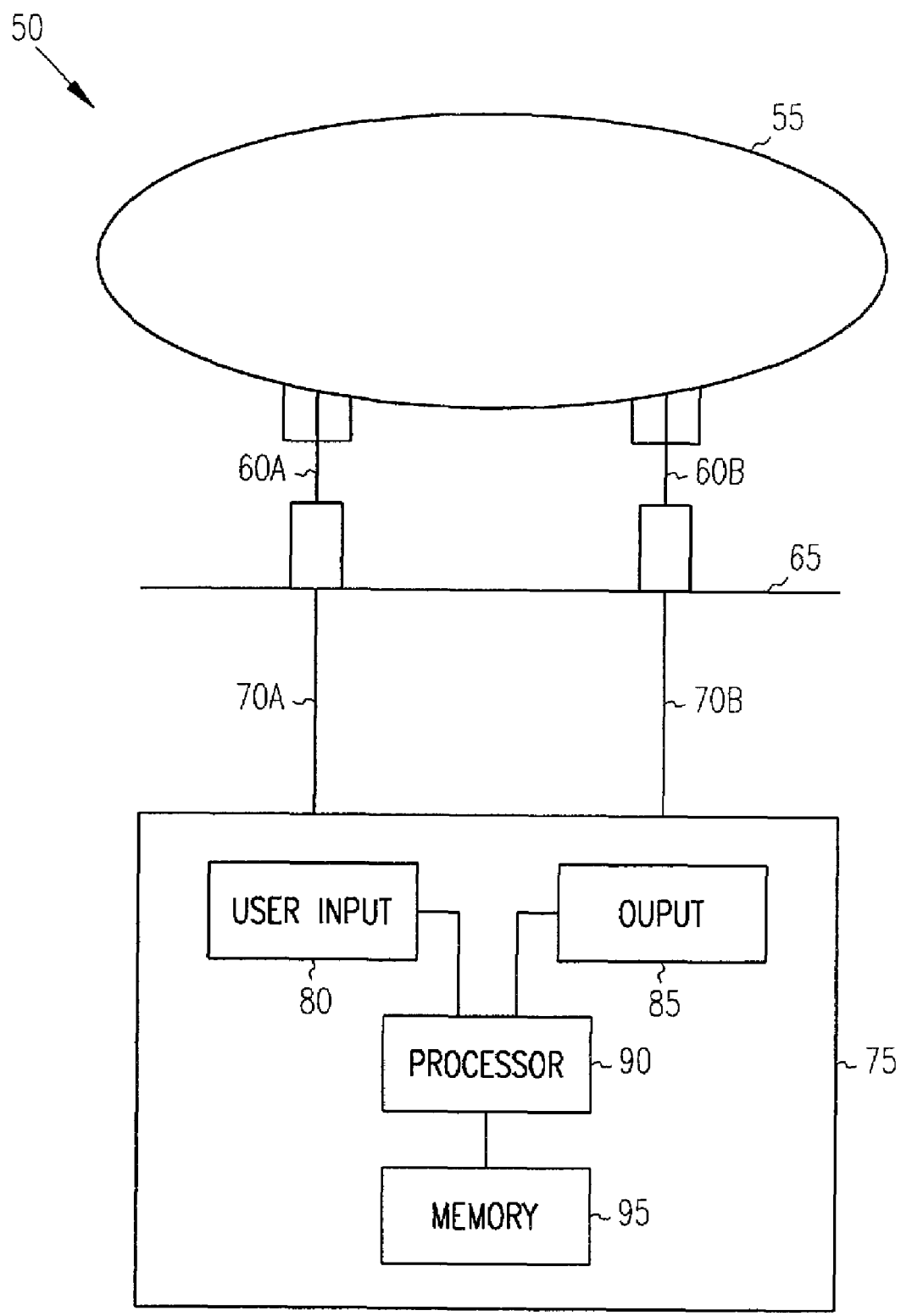
FIG. 7 is a diagram showing one embodiment of the apparatus of the invention that may be used to detect *Bacillus* bacteria or spores in a sample.
Figure 8:
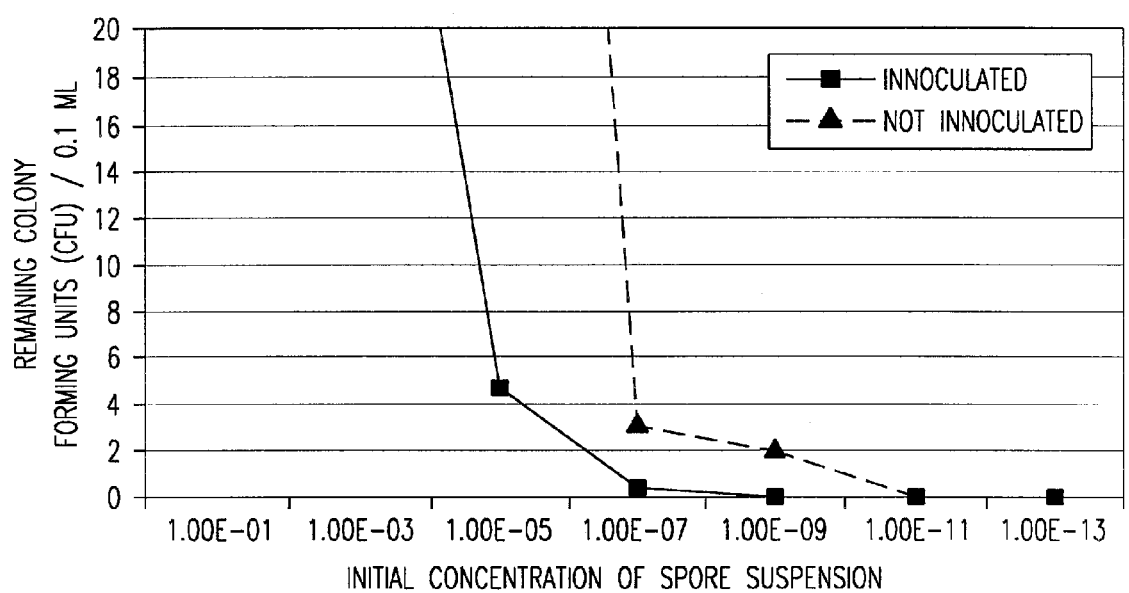
FIG. 8 illustrates bacterial liquid culture lysis using NikoA bacteriophage lysate. Overnight cultures of *B. cereus* 569 UM20 were grown in shaking flasks at 30° C. One mL of overnight culture was transferred to each of two flasks containing 20 mL NBY and each was shaken at 150 RPM for 20 minutes at 30° C. Flask 1 ('inoculated') was inoculated with 400 uL of bacteriophage NikoA (containing approximately $10^7$ PFU/mL). The same volume of NBY was added to flask 2 ('Not inoculated'). Both flasks were shaken at 30° C. for 24 hr. Spores from both cultures were harvested by separate filtration (on 0.45 um nylon filters, Fisher). The filter papers were dried and spores transferred to sterile 30 mL centrifuge tubes. Spores were washed three times in 25 mL of sterile distilled water by vortexing followed by low speed centrifugation, then were frozen. Spores from both treatment were plated out to $10^{11}$ dilution using standard spread plate methods on NBY agar media. Bacterial counts were taken after overnight growth at 37° C.

The effects of various treatments on the infectivity of bacteriophages was tested (FIG. 6). A cleared lysate was prepared that contained a community of bacteriophages. All treatments of undiluted cleared lysate were carried out in triplicate, using three replicates of each treatment. Treated bacteriophages were tested for infectivity immediately after each treatment or stored for a brief time at 4° C. Infectivity was tested by standard plaque assay (on *B. cereus* 569 UM20 or *B. anthracis* Sterne) of at least three samples from each replicate. Filtration tolerance was tested by passing 2-3 mL of lysate through 0.45 µM nylon filters (Fisher Scientific). Aerosol treatments were carried out by pumping 0.5 mL of lysate through a nasal sprayer. Lysate was pumped through a hole of 0.2 mm diameter at 0.23 mL/second. Aliquots were pumped through the sprayer into sterile glass vials. The spraying was carried out 3 times per aliquot. Temperature trials involved incubation 100 uL lysate at −20, 0, 25, 37, 55, or 65° C. for twelve hours in sealed glass tubes. Tolerance to sunligh was tested by incubation of 100 µL lysate in sealed glass tubes in direct sunlight at ambient temperature (30° C.) for four hours. The effect of sun-drying was tested by incubation of 100 µL lysate in open glass tubes in direct sunlight at ambient temperature (30° C.) for three hours. The effects of calf erythrocytes, calf serum or human perspiration was determined by incubating 100 µL of lysate with an equal volume of calf serum or erythrocytes (Colorado Serum, Denver, Colo.) or human perspiration at 37° C. for eight hours. Ultraviolet (UV) light tolerance was tested by direct exposure of 200 µL drops of lysate (on a sterile plastic petri dish) to UV light (at a distance of eight cm from a standard shortwave UV sterilization lamp (0.70 amps, Ultra-Violet Prod. Inc., San Gabriel, Calif., Model C81)).

Bacteriophage Particle Structural Protein Analysis

Figure 4:
FIG. 4 illustrates protein patterns from purified bacteriophage particles. CsCl-purified bacteriophages were denatured and separated by denaturing polyacrylamide gel electrophoresis on 12.5% acrylamide gels run at 150 volts (constant) for 55 minutes in 25 mM Tris buffer (pH 8.3). Gels were silver stained. Numbers at the right indicate protein size in kilodaltons. Letters on the top indicate lanes loaded with proteins from bacteriophages: A: CP-51; B: CP-51t; C: NikoA; D: DDBa; E: MHWa; F: SP50; G: ϕ29; and H: silver stain SDS-PAGE standards, high and low range (Biorad).

Bacteriophage particle structural protein analysis was carried out using cesium chloride step gradient purified bacteriophages (Carlson and Miller, Experiments in T4 genetics. In Molecular biology of bacteriophage T4. Edited by Karam, J. D. ASM Press, Washington D.C. pp. 432-433 (1994)), proteins from which were separated by denaturing polyacrylamide gel electrophoresis on 12.5% acrylamide gels run at 150 V (constant) for 55 min (Laemmli, *Nature*, 227:680-685 (1970)). Gels were stained using the BioRad Silver Stain Kit (BioRad, Hercules, Calif.) according to manufacturer's instructions. Protein profiles from CP-51c and CP-51t were nearly identical, differing in an approximately 48 kDa band visible in the CP-51t profile, but not visible from the CP-51c profile (FIG. 4). Other distinctions in protein profiles of the CP-51 isolates were limited mostly to intensity differences of several bands above 45 kDa. The difference between these profiles reflects differences at the level of bacteriophage strain because CP-51t arose from a purified CP-51 culture, then was maintained as a stable isolate. Bacteriophages NikoA, DDBa and MHWa all displayed a prominent doublet of approximately 50 kDa and otherwise had protein patterns distinct from CP-51. NikoA, DDBa and MHWa differed in terms of abundance and size of bands of 55-60 kDa and of 21-26 kDa. The protein profile of MHWa closely resembled that of φ29, but MHWa featured a strong doublet at about 50 kDa where φ29 displayed a single band, thus supporting placement of MHWa in the "φ29-like virus" genus. Protein profiles produced from SP50 resembled the NikoA protein profile, but differed in sizes and abundance of bands below 45 kDa.

Bacteriophage structural protein analysis was also conducted to investigate apparent similarities between NikoA, DDBa, SP50, MHWa and φ29. Bacteriophages were separated as bands in approximately 1.5 g/ml cesium chloride gradients by centrifugation in a Beckman L-70 ultracentrifuge, using an SW-55 rotor at 32,000 RPM for 2 hours at 20° C. Structural proteins of cesium chloride-purified bacteriophages were denatured by boiling for 4 minutes with sodium dodecyl sulfate and seperated by SDS-polyacrylamide gel electrophoresis on 12.5% acrylamide gels run at 150 constant volts for 65 minutes in 25 mM Tris buffer, pH 8.3. Gels were silver stained using a silver stain kit (Biorad, Hercules, Calif.) according to the manufacturer's instructions. NikoA, DDBa and MHWa all displayed prominent bands of approximately 50 kDa, but differed overall in terms of size and number of bands, especially in the range from 55 to 60 kDa. The protein profile of MHWa closely resembled that of φ29, but the MHWa profile featured one strong protein band between 66 kDa and 97 kDa, where the φ29 profile displayed a multiplicity of bands in this range. The protein profile produced from SP50 resembled that of NikoA and DDBa in the 50 kDa range, but NikoA protein was distinguished by a very prominent, sharp band of about 97 kDa, which was absent from both the DDBa and SP50 profiles. SP50 also lacked several bands of about 45 kDa that were present in both NikoA and DDBa.

Analysis of Bacteriophage DNA

Bacteriophages were pelleted by high speed centrifugation and host DNA and RNA eliminated from resuspended pellets by digestion with DNase and RNase (Carlson and Miller, Experiments in T4 genetics. In Molecular biology of bacteriophage T4. Edited by Karam, J. D. ASM Press, Washington D.C. pp. 432-433 (1994)). CP-51 DNA was obtained from resuspended bacteriophage pellets through cetyltrimethylammoniumbromide (CTAB) precipitation (Del Sal et al., *Biotechniques,* 7:514-519 (1989); Ralph and Berquist, Separation of viruses into components. In Methods in Virology. Edited by Maramorosch, K. and Koprowski, H. Academic Press, New York. pp. 463-545 (1967)). DNA was separated by pulsed field DNA electrophoresis (Steward et al., *Limnology and Oceanography,* 45:1697-1706 (2000)) at 18° C., 6 V cm$^{-1}$ for 30 h with switch time increasing from 1 to 12 seconds at a rate of 2 sec every 2 hrs, on 1% agarose gels in 0.5×TBE (tris-borate-EDTA) buffer, pH 8.3. Genomic DNA from DDBa (FIG. 5, upper left panel, approximately 80 kb) appeared slightly larger than DNA from NikoA (approximately 70 kb), both migrating below the 97 kb marker. If DDBa and NikoA are tentatively assigned to the "SP01-like virus" genus, both genomic DNAs (less than 97 kb) are small for the genus (140-160 kb). MHWa DNA migrated just below the 23.1 kb marker as expected for a "φ29-like" bacteriophage. CP-51c and CP-51t DNAs consistently displayed 6-8 bands in electrophoretic separation (pulsed field or standard gels, FIG. 5, upper panels), the top band of which measured approximately 20 kb in size (pulsed field gel, FIG. 5, upper left panel). The set of 3 DNA bands between 9.4 and 4.3 kb measured approximately 8, 7 and 5.5 kb (top to bottom), which sums to 20.5 kb. The smaller "fragments" are consistent with DNA from partially filled heads or partial DNA extrusion accompanying "premature" tail contraction (in the absence of host contact). CP-51 lability is thought to result from such tail contraction under cold conditions and electron micrographs depicting the contracted tails have been previously published (Thorne and Holt, *J. Virol.,* 14:1008-1012 (1974)).

The DNA from purified particles is suggested to be "what is left" in bacteriophage particles after a substantial proportion of the bacteriophage population has undergone the contractile conformational shift and the extruded DNA has been digested by DNase during bacteriophage purification for DNA analysis. The intensities of the bands in the profile suggests that a low proportion of the particles in a sample contain whole, genomic DNA (ca. 20 kb). The sizes of the smaller DNA "fragments" were consistent over many DNA preparations, so the extrusion of CP-51 DNA may occur through a series of "discrete" steps, leaving predictable lengths of DNA in the bacteriophage particle. Although micrographs of both NikoA and DDBa showed strong evidence of contracted tails, DNA from these isolates did not show any evidence of fragmentation.

Figure 5A:
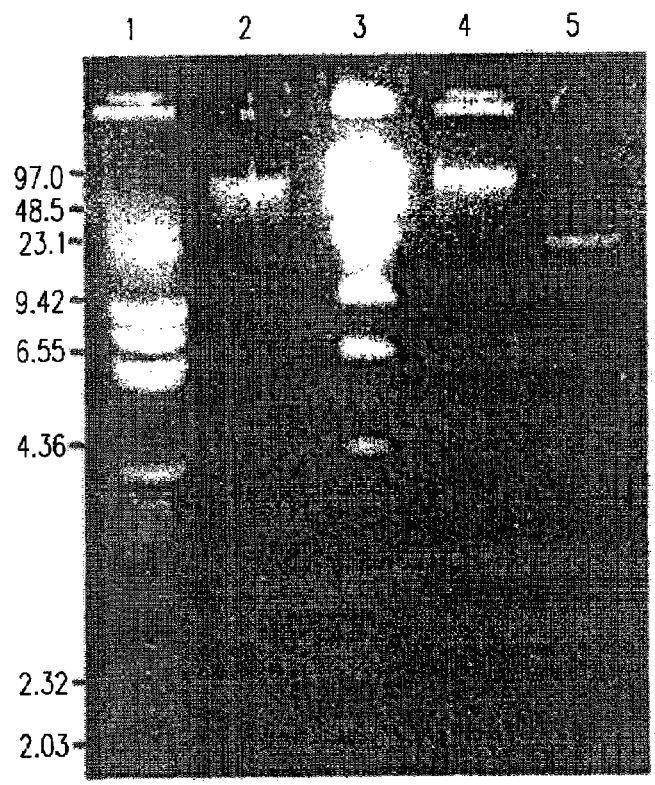
FIG. 5 illustrates an agarose gel electrophoretic separation of bacteriophage DNAs isolated using CTAB methodologies. Upper left—pulsed field gel electrophoretic separation of bacteriophage DNAs in 1% agarose gels in 0.5×TBE buffer (pH 8.3) at 18° C., 16 $V/cm^{-1}$ for 30 hours. Lanes were loaded with DNA from 1:CP-51c; 2: NikoA; 4:DDBa and 5: MHWa. Lane 3 contains Low Range PFG Marker DNA (New England Biolabs). Numbers at left indicate DNA size in kilobases (kb). Upper right—standard 1% agarose gel electrophoresis of CP-51 DNA in 0.5×TBE (pH 8.3). Lanes were loaded with DNA from: 1:1 kb ladder (Promega) size markers; 2: CP-51c DNA; 3: CP-51t DNA. Numbers at left indicate DNA size in kilobases (kb). Lower–Susceptibility of bacteriophage DNA to restriction endonuclease digestion. Standard 1% agarose gel electrophoresis in 0.5×TBE (pH 8.3) of bacteriophage genomic DNA following 1 hour digestion. Marker indicates position of undigested genomic DNA. Bacteriophage DNA sources: C, N, D and M: CP-51, NikoA, DDBa & MHWa respectively. Restriction enzymes: E: Eco RI; S: SacI; X: XbaI.
Figure 5B:
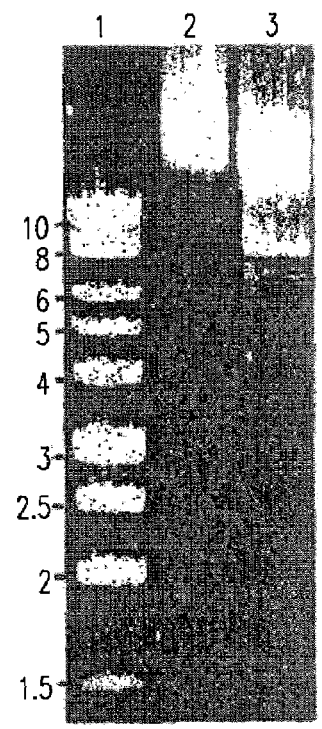
Figure 5C:
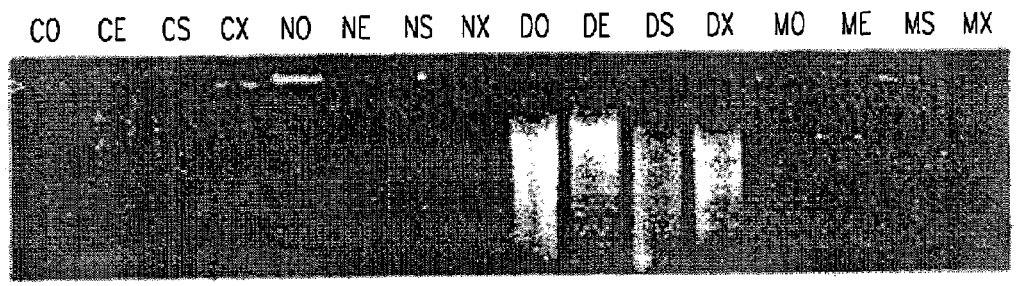

It was observed that the "genomic" DNA of CP-51c appeared somewhat larger than that of CP-51t in standard electrophoresis gels (1% agarose, 0.5×TBE, FIG. 5, upper right panel). The 3 DNA bands between 9 and 4 kb of CP-51c appeared to match the pulsed field gel size estimates. The corresponding DNA bands from CP-51t all appeared approximately 1 kb smaller, as did minor bands below 4 kb. Certain isolates of C1-51 c would occasionally give rise to a small proportion of turbid plaques, but CP-51t isolates never gave rise to clear plaques. Overall, these observations are consistent with the possibility of a deletion in CP-51c having given rise to CP-51t and the loss of the ability to form a clear plaque. All bacteriophages were susceptible to digestion by restriction endonucleases. In addition to digestion with Eco RI, Sac I and Xba I (FIG. 5, lower panel), CP-51 demonstrated additional susceptibility to digest by Kpn I, Xma I and Hinc II (not shown). All enzymes cut too frequently to allow mapping or assist size determination of CP-51 genomic DNA by large fragment analysis. FIGS. 5 and 14-17 demonstrate that restriction digestion and mapping of DNA from bacteriophages NikoA, DDBa and MHWa is possible.

Figure 14A:
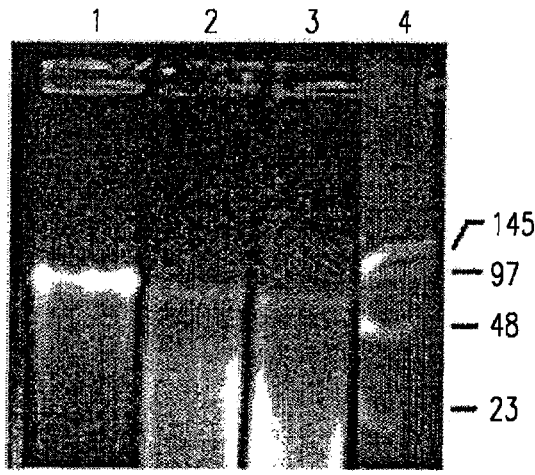
FIG. 14 illustrates the agarose gel electrophoretic separation of bacteriophage DNA isolated from bacteriophages by cetyltrimethylammonium bromide precipitation (Del Sal et al. 1989 and Ralph and Berquist 1967). A. Pulsed field gel electrophoretic (PFGE) separation of phage DNA in 1% agarose gels in 0.5×TBE buffer, pH 8.3 at 4° C., 6 V cm$^{-1}$ and a 120° included angle for 24 h with a 1-12 s switch time (ramped up from 1 s at 1 sec/2 h). Lanes were loaded with DNA from: 1, DDBa; 2, SP50; and 3, NikoA. Lane 4 contains Low Range PFG Marker DNA (New England BioLabs, Beverly, Mass.). Numbers at left indicate DNA size in kilobases. B. PFGE separation of bacteriophage DNA as in A, but for 15 h (with a 1-7 s switch time). Lanes were loaded with DNA from: 1, φ29; 2, MHWa. Lane 3 contains Low Range Marker DNA, as in A. Numbers at left indicate DNA size in kilobases. C. Electrophoretic separation (non-pulsed field) of bacteriophage DNA subjected to restriction endonuclease digestion. Standard 1% agarose gel electrophoresis (as above) of bacteriophage genomic DNA following an 8 hour digestion by restriction endonuclease Eco RI (Promega, Madison, Wis.) at 37° C. according to manufacturers instructions. Lanes 1, 3, 5, 8 and 10 were loaded with DNA from NikoA, SP50, DDBa, MHWa, and φ29 respectively. Lanes 2, 4, 6, 9 and 11 were loaded with Eco RI-treated DNA from NikoA, SP50, DDBa MHWa, and φ29 respectively. Lane 12 contained '1 kb DNA Ladder' (Promega) size markers. Numbers at left indicate DNA size in kilobases (kb).
Figure 14B:
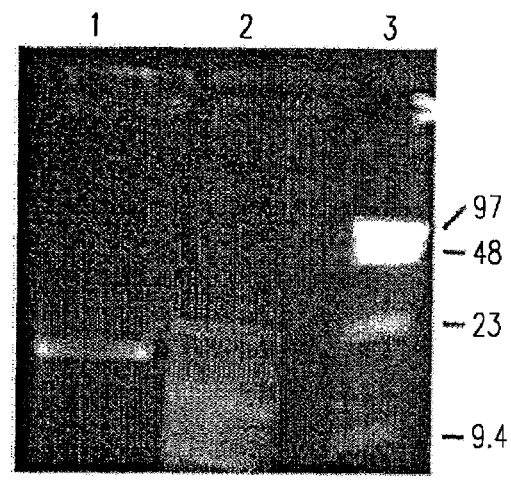
Figure 14C:
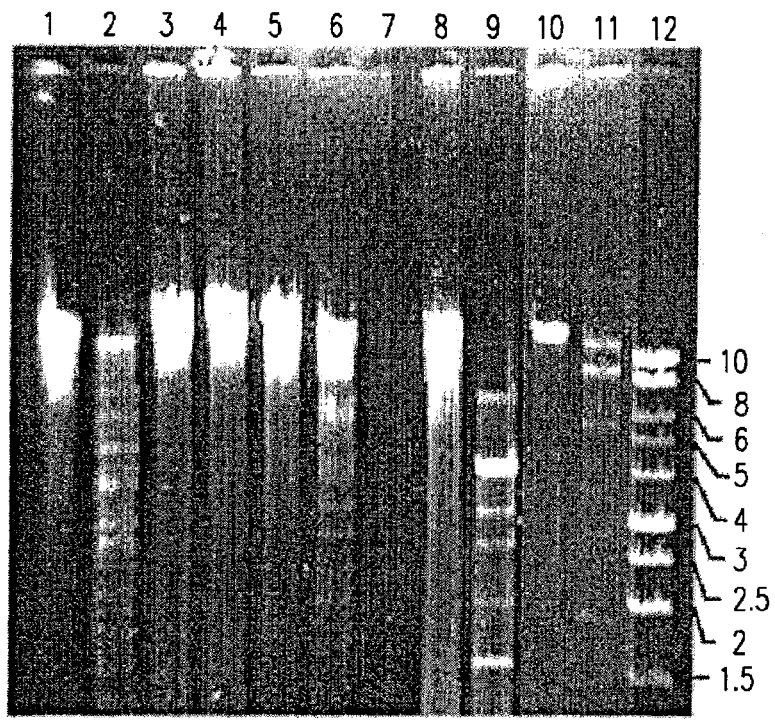

Additional restriction digestion was conducted on bacteriophages NikoA, DDBa and MHWa (FIG. 14). Bacteriophage DNA was obtained from bacteriophages purified through one round of differential centrifugation and subjected to cetyltrimethylammonium bromide (CTAB) DNA precipitation (Del Sal et al., *Biotechniques,* 7: 514-519 (1989); Ralph and Berquist, Separation of viruses into components. In Methods in Virology. Edited by Maramorosch, K. and Koprowski, H. Academic Press, New York. pp. 463-545 (1967)). DNA was separated by a pulsed field DNA electrophoresis procedure modified from Steward (Steward et al., *Limnology and Oceanography,* 45: 1697-1706 (2000)). Electrophoresis was carried out at 4° C., 6 volts cm$^{-1}$ for 15-20 hours with switch time increasing from 1 to 12 seconds at a rate of 1 second every 2 hours, on 1% agarose gels in 0.5×TBE (tris-borate-ethylemediaminetetraacetate (EDTA) buffer), pH 8.3. DNA from DDBa (FIG. 14A) appeared slightly larger than DNA from NikoA or SP50 which both migrated below the 97 kb marker. MHWa DNA was approximately 23 kb (FIG. 4B, migrating with the 23 kb marker) and slightly above the φ29 DNA. MHWa also displayed two additional but weak DNA bands between 9 and 20 kb.

Figure 15:
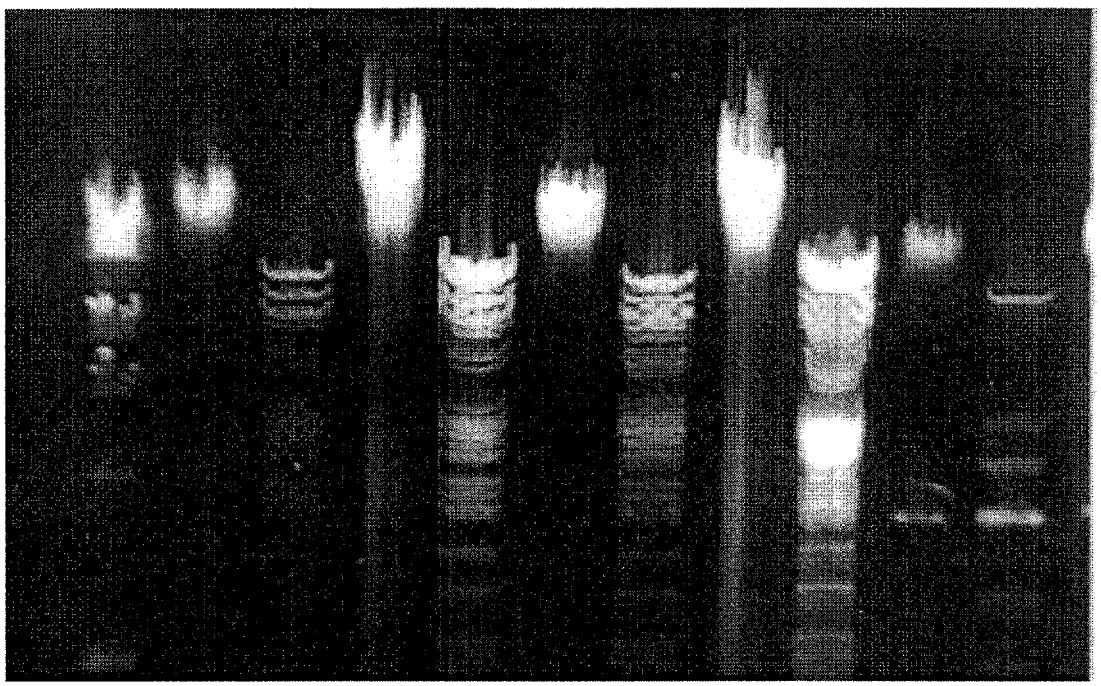
FIG. 15 illustrates restriction digestion of bacteriophage DNA from DDBa and NikoA with Eco RI. Lanes 1: Lambda digested with Hind III; 2, 4, 6 and 8: DDBa; 3, 5, 7, 9: DDBa digested with Eco RI; 10: NikoA; 11: NikoA digested with EcoRI
Figure 16:
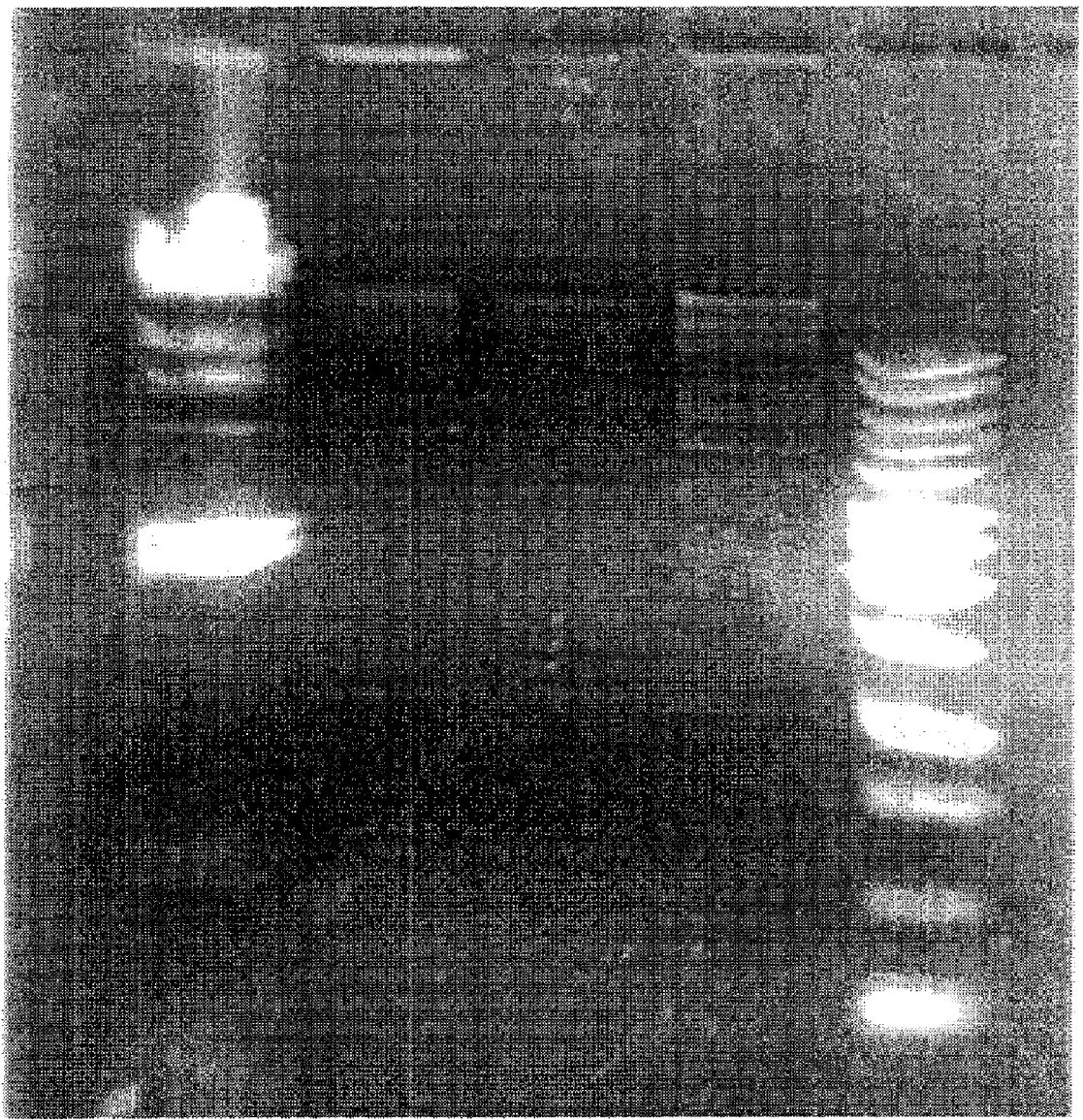
FIG. 16 illustrates restriction digestion of bacteriophage MHWa DNA with Eco RI. Lane 1: Lambda digested with Hind III; 2: MHWa; 3 and 4: MHWa digested with Eco RI; 5: 1 kb ladder (Promega) size markers.
Figure 17A:
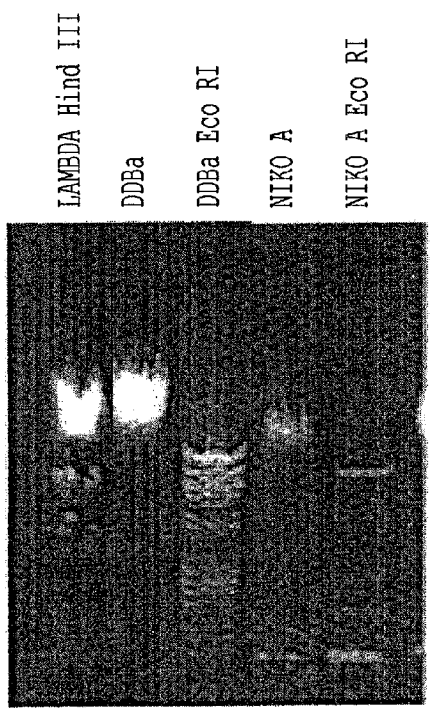
FIG. 17 illustrates restriction digestion of DNA from bacteriophages DDBa, NikoA and MHWa, undigested or digested with restriction enzyme Eco RI. Standard DNA size reference Lambda Hind III is included as left lanes in both gels as size reference. Gels are standard 1% agarose gels and electrophoresis was run at 80 V for 2 h in TBE buffer pH 7.5. Bacteriophage DNA extraction and purification is as described herein.
Figure 17B:
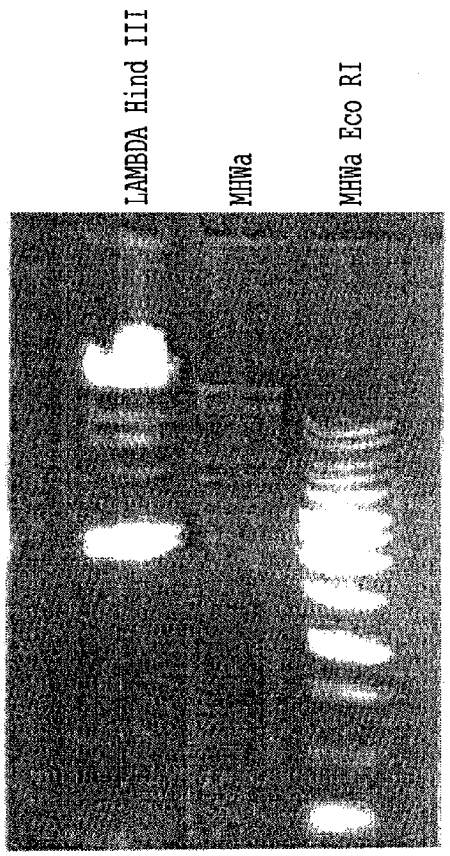

DNAs from NikoA, DDBa, MHWa and φ29 were all susceptible to digestion by restriction endonuclease Eco RI (Promega, Madison, Wis.). Electrophoretic separation (in 1% agarose, non-pulsed field electrophoresis, FIG. 14C) of bacteriophage DNA subjected to 8 hours restriction endonuclease digestion at 37° C. (according to the manufacturer's instructions) revealed that only SP50 DNA was not susceptible to digestion by Eco RI, further distinguishing it from NikoA and DDBa. The restriction pattern of Eco RI digested MHWa DNA revealed different fragments and was clearly different than the pattern from φ29. Digestion of DDBa DNA (approximately 29400 basepairs) with Eco RI produced DNA fragments of the following approximate sizes (basepairs): 18036, 14510, 11375, 9286, 7987, 7207, 4093, 3771, 3342, 2805, 2537, 2298, 2264, 2197, 2132, 2054, 1761 and 1096 (FIG. 15). Digestion of NikoA DNA (approximately 22427 basepairs) with Eco RI produced DNA fragments of the following approximate sizes (basepairs): 16801, 14691, 5679, 4690, 3934, 3057, 2309, 1973, 1611 and 1357 (FIG. 15). Digestion of MHWa DNA (approximately 19839 to 21484 basepairs) with Eco RI produced DNA fragments of the following approximate sizes (basepairs): 19290, 16547, 11062, 9026, 8117, 8373, 8020, 7737, 7180 and 6245 (FIG. 16). These restriction patterns can be used to identify bacteriophages such as NikoA, DDBa or MHWa. Endonuclease digestion of DNA with Eco RI in particular, as well as other endonucleases that are well known and commonly used in the art, will produce unique fragment patterns known as restriction mapping. Restriction mapping is a common method used to characterize and to identify nucleic acids, particularly large pieces of DNA that have not been sequenced. Such methods have also been used to characterize and identify viruses and bacteriophages such as Adenovirus-2, λ phage, M13 and φX174. Methods and materials for restriction mapping are well known in the art and are available commercially. (Watson et al., Molecular Biology of the Gene, Benjamin Cummings Publishing Company, Inc. (Menlo Park, Calif.)(1987); Sambrook et al., Molecular Cloning: A Laboratory Manual, 2nd edition, Cold Spring Harbor Press, Cold Spring Harbor, N.Y. (1989); New England Biolabs, Beverly, Mass.; Lewin, Genes VII, Oxford University Press, New York, N.Y. (2000)). Such methods generally allow the size of DNA fragments to be determined with a 10% error, preferably 5% error, and more preferably 1% error or less. (Elder et al., *Anal. Biochem.*, 128:223 (1983)).

Electron Microscopy

Bacteriophage suspensions were put on copper grids with carbon-coated Formvar films and negatively stained with 1% phosphotungstate pH 7.0 and observed in a JEOL 1200EX scanning and transmission electron microscope (FIG. 13) (Japan Electron Optics Laboratories, Boston, Mass.) at the Bessey Microscopy Facility (Department of Botany, Iowa State University, Ames, Iowa). Magnifications were controlled by use of catalase crystals (Electron microscopy Sciences, Ft. Washington, Pa.)(Luftig, *J. Ultrastruct. Res. JID-*0376344, 20:91-102 (1967)). Bacteriophage φ29 was included as an internal standard (head dimensions about 50 nm long×40 nm wide)(Ackerman and Dubow, Family Podoviridae. van Regenmortel et al. In Virus Taxonomy: Classification and Nomenclature of Viruses. Seventh Report of the International Committee on Taxonomy of Viruses. 7th Report, pp. 106-109 (2000)) in the NikoA sample examined by electron microscopy.

Analysis of Bacteriophage

The characterizations disclosed herein, including electron micrographs, host range studies, protein and genomic DNA analysis and restriction endonuclease digestion establish that NikoA, DDBa and MHWa are distinct isolates that differ from SP50 and φ29. MHWa is φ29-like and may be considered an unassigned species of the family Podoviridae. NikoA and DDBa may be considered unassigned species of the Myoviridae.

The previous work on CP-51 was extended to include DNA and protein analysis and further observations on stability. The apparent requirement for very early host log phase (for infection) and the long latent period (50 min) suggest that the latent period of CP-51 coincided with host growth somewhat later in log phase (and less susceptible to infection) and may explain why CP-51 never cleared liquid cultures. The DNA data disclosed herein suggest that the MW of CP-51 DNA is closer to 20 kb than to 84 kb (between $54.3 \times 10^6$ and $61.6 \times 10^6$ Daltons, (Yelton and Thorne, *J. Virol.*, 8: 242-253 (1971)) as first suggested before common use of DNA gel electrophoresis. Alternatively, CP-51 genomic DNA may actually be close to 84 kb in size, but particle instability prevented the full length DNA from being observed. The CP-51t and CP-51c strains are useful for investigating the molecular basis of turbid vs clear plaque formation for this bacteriophage group.

MHWa latent period is rapid and stability is relatively high. In addition, both NikoA and DDBa display characteristics that are thought to be necessary for development of bacteriophage in anti-bacterial systems. Both bacteriophages are stable, form clear plaques and can at least partially clear liquid culture. Such bacteriophages, capable of rapid attachment and lysis, are thought to be very useful in developing systems for detecting bacteria, lowering the infectivity of large bacterial cultures or assisting in decontamination efforts. Further, the characterization of bacteriophages NikoA and DDBa confirm that *B. anthracis* specific, virulent, stable bacteriophages may be isolated from natural sources.

TABLE 1

General characteristics of CP-51, NikoA, DDBa and MHWa.

| Characteristic | CP-51 | NikoA | DDBa | MHWa |
|---|---|---|---|---|
| Plaque morphology[a] | isolates clear or turbid, pinpoint | clear, no rings | clear, concentric turbidity | clear, single turbid, concentric ring |
| Plaque diameter (mm) | <1 | 1.5 | 2 | 2 |
| /speed (hours) | /8-12 h | /4-5 h | /4-5 h | /4-5 h |
| Maximum dilution allowing plate clearing | $10^2$ | $10^5$ | $10^5$ | $10^5$ |
| Typical SAP[b] culture yield, pfu[c]/mL | $3 \times 10^4$ | $3 \times 10^7$ | $4 \times 10^7$ | $3 \times 10^{10}$ |
| Latent period | 54 min | 30 min | 25 min | 35 min |
| Head diameter (nm) (average) | | 92 ± 6 | 93 ± 7 | 30 ± 2 |
| Head length (MHWa only) | | | | 50 ± 3 |
| Tail length (average) | | 180 ± 9 & 102 ± 4 | 97 ± 11 | 25 ± 4 |
| Contractile Tail? | | Yes | Yes | No |
| Number of bacteriophage measured | | 14 | 21 | 21 |

[a]clear or turbid, shape, without or with concentric rings.
[b]SAP - soft agar preparation. All isolates were prepared on over 15 occasions.
[c]pfu - plaque forming units

TABLE 2

Partial host ranges.

| Bacteria | CP-51 clear | CP-51 turbid | NikoA | DDBa | MHWa | SP50 | φ29 |
|---|---|---|---|---|---|---|---|
| B. cereus 7064 | + | + | - | - | - | - | - |
| B. cereus 55609 | + | + | + | + | - | - | - |
| B. thuringiensis 13366 | + | + | + | + | - | - | - |
| B. subtilis HWA 1243 | - | - | - | - | - | + | + |
| B. anthracis Sterne | ND | ND | + | + | + | - | - |
| B. cereus 569 UM20 | ND | ND | + | + | + | - | - |
| B. cereus 14579 | ND | ND | + | + | + | + | + |
| B. cereus var. mycoides 6462 | ND | ND | - | - | - | - | - |
| B. subtilis 1174 | ND | ND | - | - | - | - | - |
| B. megaterium 4581 | ND | ND | - | - | - | - | - |

* ND: not determined

Bacteriophage Increase

Naturally occurring soil bacteriophages were grown by incubation of 5 g topsoil (Black Hawk County, Iowa, fine ground) with 30 ml NBY (Difco Nutrient broth: 8 g/L, Difco yeast extract (Difco Laboratories, Detroit, Mich. 48232): 3 g/L, pH 6.8) broth and 3 ml log phase B. anthracis Sterne (vaccine strain, a gift from Dr. J. Jackson, Johns Hopkins University Applied Physics Laboratory) or 3 ml B. cereus 569 UM20 (obtained from Dr. Curtis Thorne: Univ. of Amherst, retired, courtesy of Dr. Terri Koehler: Dept. of Microbiology and Molecular Genetics, University of Texas-Houston Medical School). Mixtures were shaken at 150 RPM for 12 hours at 30° C. Mixtures were centrifuged at 10,000×g for 10 min and the supernatant stirred for 15 min with 5 mLs of chloroform, followed by an additional centrifugation (as above). Supernatant (cleared lysate) was stored at 4° C. with 1/30 vol of chloroform.

Bacteriophage Treatments

All treatments of the cleared lysate (a community of bacteriophages) were carried out in triplicate, using 3 replicates of each treatment. Treated replicates were tested for infectivity immediately after each treatment or stored for a brief time at 4° C. Infectivity was tested by standard plaque assay (on *B. cereus* 569 UM20) of at least 4 samples from each replicate. Filtration tolerance was tested by passing 2-3 ml of undiluted cleared lysate through 0.45 μm nylon filters (Fisher Scientific). Aerosol/atomization treatments were carried out by pumping 0.5 mLs of undiluted cleared lysate through a nasal aerosol sprayer. Cleared lysate was pumped through a hole of 0.2 mm diameter at 0.23 mLs/sec. Aliquots were pumped through the sprayer into sterile glass vials. The spraying was carried out 3 times per aliquot. Temperature trials involved incubating 100 μl cleared lysate at −20, 0, 25, 37, 55 or 65° C. for 12 hrs in sealed glass tubes. Tolerance to sunlight was tested by incubation of 100 μl cleared lysate in sealed glass tubes in direct sunlight at ambient temperature (30° C.) for 4 hours. The effect of sun-drying was tested by incubation of 100 μl cleared lysate in open glass tubes in direct sunlight at ambient temperature (30° C.) for 3 hours. The effects of calf erythrocytes, calf serum or human perspiration was determined by incubating a 100 μl of cleared lysate with an equal volume of calf serum or erythrocytes (Colorado Serum, Denver, Colo.) or human perspiration (supplied by the author) at 37° C. for 8 hours. Ultraviolet (UV) light tolerance was tested by direct exposure of 200 μl of cleared lysate (large drops on plastic petri dishes) to UV light (at a distance of 10 cm from a standard Shortwave UV Sterilization Lamp (0.70 amps, Ultra-Violet Prod. Inc., San Gabriel, Calif., Model C81).

Bacteriophage Description

Although NikoA and DDBa resemble SP50 in morphology, host range studies, protein and DNA suggest that both differ from SP50. NikoA and DDBa can be assigned to the "SP50-morphotype", but are distinct in terms of host range, structural protein and DNA. NikoA and DDBa may be considered as SP50-like unassigned members if the Myoviridae family. Based on morphology, MHWa belongs in the family Podoviridae, φ29 group, but is a separate strain based on host range and protein analysis.

Titres of naturally occurring soil bacteriophages were approximately $10^{10}$ plaque forming units (PFU)/ml whether increased on *B. anthracis* Sterne or *B. cereus*.

The infectivity of the *B. cereus* bacteriophage community proved surprisingly resilient and retained the ability to lyse *B. cereus* following most treatments (FIG. 6). The cleared bacteriophage lysate was most sensitive to drying, high temperatures and prolonged direct sunlight. The bacteriophages survived filtration, aerosolization and treatments with various body fluids. Calf serum and UV treatment both reduced infectivity by about an order of magnitude. Incubation at 55° C. reduced infectious titre considerably, while 65° C. or 80° C. deactivated bacteriophage completely (not shown). Sun drying also completely eliminated infectivity (not shown). Aerosolization, 25° C. treatment and treatment with erythrocytes all appeared to increase the infectivity of the cleared lysate.

The above tests demonstrate that natural populations of *B. cereus/anthracis* bacteriophages contain members that maintain infectivity under conditions bacteriophages might experience if deployed as anti-bacterials. These tests ensure that expensive animal testing of bacteriophage can be focused on the bacteriophage candidates best suited to the application. Additional screens may be used for particular applications, such as electronic sampler/detectors or specialized decontamination formulations. Bacteriophage may also be selected to withstand particular combinations of factors by use of "selection" steps, incorporating the conditions of interest during bacteriophage increase to select for variants resistant to those conditions.

There are factors that may be considered when subjecting a wild, presumably diverse bacteriophage community to selective screenings. One consideration is whether the treatment alters infectivity. Another consideration is whether the treatment affects bacteriophage diversity or species richness. Given the direction and guidance of the present disclosure, coupled with what is known in the art, one of skill in the art is well equipped to respond to these factors.

DOCUMENTS

Ackermann and Dubow, Family Podoviridae. van Regenmortel et al. In Virus Taxonomy: Classification and Nomenclature of Viruses. Seventh Report of the International Committee on Taxonomy of Viruses. 7th Report, pp. 106-109 (2000).

Adams. M. H., *Bacteriophages*, New York, Interscience Publishers, Inc., (1959).

Akimkin et al., *Zh Mikrobiol Epidemiol Immunobiol.*, 85-86 (1998).

Alisky et al., *J. Infect.*, 36, 5-15 (1998).

Barrow et al., *Clin Diagn Lab Immunol.*, 5, 294-298 (1998).

Barrow and Soothill, *Trends Microbiol.*, 5, 268-271 (1997).

Biswas et al., *Infect. Immun.*, 70: 204-210 (2002).

Carlson and Miller, Experiments in T4 genetics. In Molecular biology of bacteriophage T4. Edited by Karam, J. D. ASM Press, Washington D.C. pp. 432-433 (1994a).

Carlson and Miller, Working with T4. In Molecular biology of bacteriophage T4. Edited by Karam, J. D. ASM Press, Washington D.C. pp. 421-437 (1994b).

Cowles and Hale, *Journal of Infectious Diseases*, 49: 264-269 (1931).

d'Herelle, *C R Acad Ser D*, 165, 373 (1917).

Del Sal et al., *Biotechniques*, 7: 514-519 (1989).

Eiserling and Boy de la Tour, *Path. Microbiol.*, 28: 175-180 (1965).

Elder et al., *Anal. Biochem.*, 128:223 (1983)

Ellis and Delbrück, *J. Gen. Physiol.*, 22: 365-384 (1939).

Fox, *ASM News*, 66[8], 455-456 (2000).

Helgason et al., *Appl Environ Microbiol*, 66, 2627-2630 (2000).

Holt, J. G. Bergey's Manual of Systematic Bacteriology. Baltimore, Williams & Wilkins (1984).

Hughes et al., *Appl. Environ. Microbiol.*, 68:4399 (2001).

Kortepeter and Parker, *Emerg Infect Dis*, 5, 523-527 (1999).

Kudva et al., *Appl Environ Microbiol.*, 65: 3767-3773 (1999).

Kutter, E., Phage Therapy: Bacteriophages as antibiotics: Update http://www evergreen edu/user/T4/PhageTherapy (2000).

Laemmli, U. K., *Nature*, 227: 680-685 (1970).

Lederberg, J., *Proc Natl Acad Sci USA*, 93: 3167-3168 (1996).

Leverentz et al., *J Food Prot*, 64, 1116-1121 (2001).

Levin and Bull, *The American Naturalist*, 147: 881-898 (1996).

Lewin, Genes VII, Oxford University Press, New York, N.Y. (2000).

Luftig, R., *J. Ultrastruct. Res. JID*-0376344, 20:91-102 (1967).

Marshall, E., *Science*, 289, 382-383 (2000).

Merril, C. R., *Trans NY Acad Sci*, 36, 265-272 (1974).

Merril et al., *Proc Natl Acad Sci USA*, 93, 3188-3192 (1996).

Ralph and Berquist, Separation of viruses into components. In Methods in Virology. Edited by Maramorosch, K. and Koprowski, H. Academic Press, New York. pp. 463-545 (1967).

Sambrook et al., Molecular Cloning: A Laboratory Manual, 2nd edition, Cold Spring Harbor Press, Cold Spring Harbor, N.Y. (1989).

Steward et al., *Limnology and Oceanography* 45: 1697-1706 (2000).

Sulakvelidze et al., *Antimicrob Agents Chemother*, 45, 649-659 (2001).

Thorne, C. B., *J. Virol.*, 2: 657-662 (1968a).

Thorne, C. B., *Bacteriol Rev.*, 32: 358-361 (1968b).

Thorne and Holt, *J. Virol.*, 14: 1008-1012 (1974).

Twort, F. W., *Lancet*, 1241-1243 (1915).

van Regenmortel et al., Virus taxonomy, 7th report of the International Committee on Taxonomy of Viruses. Edited by van Regenmortel, M. H. V., Fauquet, C. M., Bishop, D. H L., Carstens, E. B., Estes, M. K., Lemon, S. M., Maniloff, J., Mayo, M. A., McGeoch, D. J., Pringle, C. R., and Wickner, R. B. Academic Press, San Diego. pp. 43-52 (2000).

Van Tassel and Yousten, *Can J Microbiol.*, 22: 583-586 (1976).

Watson et al., Molecular Biology of the Gene, Benjamin Cummings Publishing Company, Inc. (Menlo Park, Calif.) (1987);

Weber-Darowska et al., *Arch Immunol Ther Exp* (Warsz), 48, 31-37 (2000).

Yelton and Thorne, *J. Bacteriol.*, 102: 573-579 (1970).

Yelton and Thorne, *J. Virol.*, 8: 242-253 (1971).

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

The invention claimd is:

1. An isolated bacteriophage selected from the group consisting of NikoA (ATCC accession number PTA-4171), DDBa (ATCC accession number PTA-4172), and MHWa (ATCC accession number PTA-4173).

2. An antibacterial nutrient broth containing al least one bacteriophage selected from NikoA (ATCC accession number PTA-4171), DDBa (ATCC accession number PTA-4172), and MHWa (ATCC accession number PTA-4173).

3. A pharmaceutical composition comprising a bacteriophage selected from the group consisting of NikoA (ATCC accession number PTA-4171), DDBa (ATCC accession number PTA-4172) and MHWa (ATCC accession number PTA-4173), and a pharmaceutically acceptable carrier.

4. The composition of claim 3, wherein the pharmaceutically acceptable carrier is an aerosol, a paste, a powder, or an injectable formulation.

5. A kit comprising a bacteriophage selected from NikoA (ATCC accession number PTA-4171), DDBa (ATCC accession number PTA-4172), and MHWa (ATCC accession number PTA-4173).

6. A bacteriophage of claim 1, wherein the bacteriophage is coupled to a detectable marker.

7. The bacteriophage of claim 6, wherein the detectable marker is an enzyme, a fluorescent tag, a radioactive tag or a colorimetric tag.

8. The bacteriophage of claim 1, wherein said bacteriophage infects *Bacillus anthracis*.

9. A recombinant bacteriophage comprising the genome of NikoA (ATCC accession number PTA-4171), DDBa (ATCC accession number PTA-4172), or MHWa (ATCC accession number PTA-4173), wherein said genome comprises an exogeneous nucleic acid.

10. The recombinant bacteriophage of claim 9, wherein the exogeneous nucleic acid encodes a drug resistance gene.

11. The recombinant bacteriophage of claim 1, wherein the drug is tetracycline, ampicillin, streptomycin or rifampicin.

12. The recombinant bacteriophage of claim 9, wherein the exogeneous nucleic acid is an expression cassette.

13. The recombinant bacteriophage of claim 12, wherein the expression cassette comprises a regulatory sequence.

14. The recombinant bacteriophage of claim 13, wherein the regulatory sequence is a *Bacillus* promoter.

15. A pharmaceutical composition comprising the recombinant bacteriophage of claim 9, and a pharmaceutically acceptable carrier.

16. The pharmaceutical composition of claim 15, wherein the pharmaceutically acceptable carrier is an aerosol, a paste, a powder, or an injectable formulation.

17. An antibacterial nutrient broth containing at least one bacteriophage, wherein at least one bacteriophage is the recombinant bacteriophage of claim 9.

18. A kit comprising the bacteriophage of claim 9.

* * * * *